United States Patent
Dhakal et al.

(10) Patent No.: US 11,441,182 B2
(45) Date of Patent: Sep. 13, 2022

(54) MULTIPLEXED AND RECYCLABLE SINGLE-MOLECULE SENSORS FOR QUANTITATIVE ANALYSIS OF NUCLEIC-ACID BIOMARKERS

(71) Applicant: Virginia Commonwealth University, Richmond, VA (US)

(72) Inventors: Soma Dhakal, Glen Allen, VA (US); Anisa Kaur, Hanover, VA (US)

(73) Assignee: Virginia Commonwealth University, Richmond, VA (US)

( * ) Notice: Subject to any disclaimer, the term of this patent is extended or adjusted under 35 U.S.C. 154(b) by 405 days.

(21) Appl. No.: 16/535,722

(22) Filed: Aug. 8, 2019

(65) Prior Publication Data

US 2020/0048710 A1 Feb. 13, 2020

Related U.S. Application Data

(60) Provisional application No. 62/716,198, filed on Aug. 8, 2018.

(51) Int. Cl.
*C12Q 1/6876* (2018.01)
*G01N 21/64* (2006.01)

(52) U.S. Cl.
CPC ....... *C12Q 1/6876* (2013.01); *G01N 21/6428* (2013.01)

(58) Field of Classification Search
CPC ...... C12Q 1/68; C12Q 1/6876; C12Q 1/6816; C12Q 2525/301; G01N 21/6428; C12M 1/00
See application file for complete search history.

(56) References Cited

U.S. PATENT DOCUMENTS

| | | | | | |
|---|---|---|---|---|---|
| 5,424,413 | A | * | 6/1995 | Hogan | C12N 15/1068 435/6.1 |
| 5,866,336 | A | * | 2/1999 | Nazarenko | C12Q 1/686 435/6.12 |
| 2002/0197630 | A1 | * | 12/2002 | Knapp | C12Q 1/6813 435/6.11 |
| 2005/0019776 | A1 | * | 1/2005 | Callow | C12Q 1/6855 435/6.11 |
| 2009/0275632 | A1 | * | 11/2009 | Esteller | C12Q 1/6809 514/44 A |
| 2010/0144836 | A1 | * | 6/2010 | Van Engeland | A61P 35/04 514/44 A |
| 2010/0280105 | A1 | * | 11/2010 | Vlassenbroeck | A61K 39/001186 514/44 R |
| 2012/0039993 | A1 | * | 2/2012 | Otto | A61P 35/00 424/450 |
| 2020/0048710 | A1 | * | 2/2020 | Dhakal | C12Q 1/6876 |

OTHER PUBLICATIONS

Christian et al., PNAS 106(50) :21109-2114 (Year: 2009).*
Dutta et al., JACS 136 :16618-16625 (Year: 2014).*
Geibler and Hidebrandt et al. Anal. Bioanal. Chem. 408:4475-4483 (Year: 2016).*
Heid et al., Genome Research 6:986-994 (Year: 1996).*
Jungmann et al., Nano Letters 10:4756-4761 (Year: 2010).*
Jungmann et al., Nature Methods 11(3) :313 (Year: 2014).*
Kapanidas et al., PNAS 101(24) : 8936-8941 (Year: 2004).*
Kaur et al., Trends in Analytical Chemistry 123 :115777 (Year: 2020).*
Kaur et al., ACS Sensors 4: 623-633 (Year: 2019).*
Lee et al., Biophysical J. 92: 303-312 (Year: 2007).*
Lee et al., Biosensors and Bioelectronics 86:202-210 (Year: 2016).*
Shu et al., ACS Nano 4(11) :6843-6853 (Year: 2010).*
Song et al., Applied Materials & Interfaces 4 :2885-2890 (Year: 2012).*
Stein et al., JACS 133:4193-4195 (Year: 2011).*
Yang et al., NanoBioimaging 2013 :13-24 (Year: 2013).*
Yao et al., Molecular-beacon-based array for sensitive DNA analysis. Analytical Biochemistry 331 :216-223 (Year: 2004).*

* cited by examiner

*Primary Examiner* — Ethan C Whisenant
(74) *Attorney, Agent, or Firm* — Thomas | Horstemeyer, LLP

(57) ABSTRACT

Disclosed herein is a simple, sensitive, and fully-recyclable fluorescence resonance energy transfer (FRET)-based multiplex detection platform that overcomes current requirements of complex labeling schemes and complicated data analysis algorithms for employing single-molecule FRET (smFRET) microscopy in multiplexing. While conventional smFRET detection techniques allow for the analysis of one target at a time, the disclosed approach utilizes the gaps between high- and low-FRET signals to provide simultaneous detection and quantification of multiple nucleic acid targets.

11 Claims, 27 Drawing Sheets

Specification includes a Sequence Listing.

MULTIPLEXED AND RECYCLABLE SINGLE-MOLECULE SENSORS FOR QUANTITATIVE ANALYSIS OF NUCLEIC-ACID BIOMARKERS

CROSS-REFERENCE TO RELATED APPLICATIONS

This application claims benefit of U.S. Provisional Application No. 62/716,198, filed Aug. 8, 2018, which is hereby incorporated herein by reference in its entirety.

SEQUENCE LISTING

This application contains a sequence listing filed in electronic form as an ASCII.txt file entitled "322203-1050 Sequence Listing_ST25" created on Aug. 8, 2019. The content of the sequence listing is incorporated herein in its entirety.

BACKGROUND

Multiplex assays allow for the simultaneous detection of multiple analytes, help improve the diagnostic capacity of testing, save time, expense, and other resources associated with the analysis (Wang, Q., et al. (2014) Chem. Commun. 50:3824-3826; Elnifro, E. M., et al. (2000) Microbiol. Rev. 13:559-571; Kingsmore, S. F. (2006) Nat Rev Drug Discov. 5:310-320). For this reason, multiplexing is an attractive technique, especially in the field of diagnostics and biotechnology where multiplex detection of biomarkers is an ongoing feat (Huang, Y., et al. (2017) Proteomics & Bioinformatics 15:73-81). For example, it has been shown that the accuracy of diagnosis increases from as low as 65% to over 94% by measuring the level of 3 to 5 different types of biomarkers instead of just one (Wei, F., et al. (2009) Cancer Res. 15:4446-4452; Oikonomopoulou, K., et al. (2008) Br J Cancer 99:1103-1113; Mo, M.-H., et al. (2012) J Cancer 3:432-448; Li, Y., et al. (2004) Clin. Cancer Res. 10:8442). Although microarrays are the first technologies capable of parallel analysis of hundreds of analytes simultaneously from one sample, they are only semi-quantitative. For example, in fluorescence-based microarrays, an absolute intensity observed on a particular spot of a microchip is meaningless from a quantitative point of view since with the current stage of array technologies it is not feasible to create calibration curves for hundreds of targets (Kodadek, T. (2001) Chemistry & Biology 8:105-115; Berthuy, O. I., et al. (2016) Lab on a Chip 16:4248-4262). Additionally, these parallel-array techniques, including synthetic nanopores and DNA barcodes, are limited by the need for precise and sophisticated design/engineering (Kodadek, T. (2001) Chemistry & Biology 8:105-115; Wong Koon, H., et al. (2013) Curr Protoc Mol Biol. 101:7.11; Sze, J. Y. Y., et al. (2017) Nature Commun. 8:1552). While there have been many strides in producing ultrasensitive, target-specific, and low-cost multiplex assays such as fluorescent microbeads and multiplex polymerase chain reaction (PCR), these methods utilize ensemble measurements, which typically suffer from significant false positives (Gunderson, K. L., et al. (2005) Nature Genetics 37:549). In addition, the vast majority of these multiplexed methods require that targets must be labeled or modified to enable detection (Churchill, G. A. (2002) Nature Genet. 32:490; Dunbar, S. A. (2006) Clinica Chimica Acta 363:71-82). Although other popular multiplexing methods such as surface enhanced Raman spectroscopy (SERS), electrochemical biosensor, and force-based and fluorescence-based techniques involving quantum dots can overcome this drawback by labeling/modifying a probe instead of target (Kang, D., et al. (2012) Npg Asia Materials 4:e1; Geiss, G. K., et al. (2008) 26:317; Lin, C., et al. (2012) 4:832; Zhang, D. Y., et al. (2012) Nature Chemistry 4:208; Jungmann, R., et al. (2014) Nature Methods 11:313; Yang, D., et al. (2016) Nature Commun. 7:11026; Stender, A. S., et al. (2013) Chemical Rev. 113:2469-2527), there is a limit to how many non-overlapping redox/fluorescent labels can be used to resolve the multiplexed data. Unlike commonly used ensemble techniques, single-molecule FRET (smFRET) provides a slew of information about the behavior of individual molecules (Roy, R., et al. (2008) Nature Methods 5:507; Shu, D., et al. (2010) ACS Nano 4:6843-6853; Lerner, E., et al. (2018) Science 359(6373); Phelps, C., et al. (2017) Proc. Natl. Acad. Sci. USA 114:E3612; Christian, T. D., et al. (2009) Proc. Natl. Acad. Sci. USA 106:21109). However, the emerging paradigm of multiplexed sensing based on smFRET requires complicated labeling-schemes such as "antenna" or "surplus" systems (Bunt, G., et al. (2017) Biophysical Rev. 9:119-129; Stein, I. H., et al. (2011) J. Am. Chem. Soc. 133:4193-4195; Dutta, P. K., et al. (2014) J. Am. Chem. Soc. 136:16618-16625) and sophisticated numerical algorithms to analyze and interpret the data (Kapanidis, A. N., et al. (2004) Proc. Natl. Acad. Sci. USA 101:8936; Lee, N. K., et al. (2007) Biophysical Journal 92:303-312).

SUMMARY

Disclosed herein is a hairpin-based sensor that involves:

a first single-stranded oligonucleotide ("first oligo") having a 5' end and a 3' end and comprising a nucleic acid sequence that can form a hairpin with a stem and a loop that is flanked by a 5' flanking region and a 3' flanking region;

a second single-stranded oligonucleotide ("second oligo") having a 5' end and a 3' end and comprising a nucleic acid sequence complementary to at least a portion of the 3' flanking region;

a third single-stranded oligonucleotide ("third oligo") having a 5' end and a 3' end and comprising a nucleic acid sequence complementary to at least a portion of the 5' flanking region;

a fourth single-stranded oligonucleotide ("probe") having a 5' end and a 3' end, comprising a nucleic acid sequence complementary to at least a portion of the DNA hairpin region, and comprising a nucleic acid sequence complementary to a significant portion of a target DNA or RNA molecule;

a first fluorescent molecule conjugated to the second oligo; and a second fluorescent molecule conjugated to the third oligo;

wherein the first fluorescent molecule and the second fluorescent molecule together form a fluorescence resonance energy transfer (FRET) pair, wherein the FRET pair emit at a first-FRET efficiency when the probe is binding the DNA hairpin region, and wherein the FRET pair emit at a higher second-FRET efficiency when the probe binds the target DNA or RNA molecule, displacing the probe from the DNA hairpin region, allowing the hairpin region to form a hairpin, and shortening the distance between the first fluorescent molecule and the second fluorescent molecule.

Nucleic acid sequences capable of forming hairpins with at least one stem and loop are known in the art and can be designed using standard methods. Although the number of nucleotides in the stem and loop regions varies based on applications, in some embodiments, the hairpin has a stem comprising two complementary sequences of at least 3, 4, 5, 6, 7, or 8 nucleotides each. In some embodiments, the hairpin has a loop that is at least 10, 11, 12, 13, 14, 15, 17, 18, 19, 20 nucleotides, including 10 to 40 nucleotides. In some embodiments, the preferred range of hairpin loop for sensing nucleic acid targets is 15 to 30 nucleotides with a 3-7 base pair stem.

In some embodiments, the hairpin region further contains spacer nucleotides between the hairpin forming nucleic acid sequence and the flanking sequences. These spacer nucleotides can be used to modify the distance between the FRET pairs when the hairpin is formed. Therefore, also disclosed is a library of hairpin-based sensors, each with different FRET pairs and/or spacing between the FRET pairs.

In some embodiments, the oligonucleotides are DNA oligonucleotides. However, other non-natural oligonucleotides are known in the art and include locked nucleic acid (LNA) oligonucleotides, peptide nucleic acid (PNA) oligonucleotides, threose nucleic acid (TNA), hexitol nucleic acid (HNA), and 2'-O-methyl RNA oligonucleotides.

In some embodiments, the first fluorescent molecule is conjugated to the 3' end of the second oligo and the second fluorescent molecule is conjugated to the 5' end of the third oligo. In some embodiments, the fluorescent molecules are conjugated to an internal nucleic acid. It is understood that the important aspect is the distance between the FRET pairs regardless of how they are conjugated to the oligonucleotides.

Fluorescent molecules that can form FRET pairs are known in the art. For example, in some embodiments, the FRET pair comprise Cy3 and Cy5. In these embodiments, Cy3 is a donor molecule, and Cy5 is an acceptor molecule. In some embodiments, the donor molecule is conjugated to the second oligo and the acceptor molecule is conjugated to the third oligo. In other embodiments, the donor molecule is conjugated to the third oligo and the acceptor molecule is conjugated to the second oligo. While Cy3 and Cy5 are a commonly used FRET pairs, any organic dyes exhibiting high photostability, significant spectral overlap between the emission spectrum of the donor and the excitation spectrum of the acceptor, and comparable quantum yields can be used as the FRET pair. Of course, it is understood that the excitation sources, filters, and dichroic mirrors of the microscope should be selected accordingly to be able to use different FRET pairs.

Additional DNA oligonucleotides can be incorporated in the sensor to conjugate it to other molecules or structures. For example, in some embodiments, the sensor further comprises a fifth single-stranded oligonucleotide ("fifth oligo") having a 5' end and a 3' end and comprising a nucleic acid sequence complementary to at least a portion of the second oligo, wherein the 3' flanking region of the first oligo and the fifth oligo together form a complementary strand for the second oligo. In some embodiments, the sensor further comprises a sixth single-stranded oligonucleotide ("sixth oligo") having a 5' end and a 3' end and comprising a nucleic acid sequence complementary to at least a portion of the third oligo, wherein the 5' flanking region of the first oligo and the sixth oligo together form a complementary strand for the third oligo. In some embodiments, the sensor further comprises a seventh single-stranded oligonucleotide ("seventh oligo") having a 5' end and a 3' end and an eighth single-stranded oligonucleotide ("eighth oligo") having a 5' end and a 3' end, wherein the seventh oligo comprises a nucleic acid sequence complementary to at least a portion of either the fifth or the sixth oligo and a nucleic acid sequence complementary to at least a portion of the eighth oligo. Again, these additional oligos can function as modules, e.g. to conjugate the sensor to other molecules. For example, in some embodiments, the eighth oligo is conjugated to a biotin molecule.

Also disclosed is a multiplexed detection system containing a plurality of unique hairpin-based sensors as described above, wherein each of the unique hairpin-based sensors has a unique probe designed to recognize a different DNA or RNA target molecule, wherein each of the unique hairpin-based sensors has a unique spacing between the first fluorescent molecule and the second fluorescent molecule when the DNA hairpin is formed, and wherein each of the unique hairpin-based sensors have the same FRET pair but emit a unique second-FRET efficiency. In some embodiments, the hairpin-based sensors are attached to a microscope slide. In some embodiments, there are at least 2, 3, 4, 5, 6, 7, 8, 9, or 10 unique hairpin-based sensors in the disclosed system. In some cases, the unique hairpin-based sensors have FRET pair spacing when hairpins are formed that differ by only 1, 2, 3, or 4 nucleotides in length. This can be accomplished in some embodiments using spacer nucleotides in the hairpin region as disclosed herein.

Also disclosed is a method for detecting a single stranded RNA or DNA target molecule in a sample that involves contacting the disclosed multiplexed detection system with the sample under conditions suitable for DNA/RNA binding, exciting the FRET pair with a light source, and measuring FRET efficiency.

The disclosed method can be used to detect any single stranded DNA or RNA molecule. In some embodiments, the target molecule is a microRNA. In other embodiments, the target molecules can be cell-free DNA (cfDNA), circulating cf DNA, messenger RNA (mRNA), or other synthetic nucleic acids.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A (left) shows conventional approach that allows the detection of only one target. FIG. 1A (right) shows approach for simultaneous detection of multiple targets by filling the unutilized spaces (FRET gaps). P=probe, T=target. FIG. 1B shows working principle of iHabS. The probe bound iHabS with a low-FRET state (open conformation) switches to a high-FRET (closed conformation) in the presence of target DNA forming a dsDNA by-product. iHabSs are designed to be recyclable upon alternate addition of probe and target. An alternate labeling scheme for Cy3 is highlighted and referred to as "INT". FIG. 1C shows hairpins (HP) with various flanking thymine spacers (represented as the number of thymine nucleotides "nt") used to tune the FRET. The length of the thymine spacers (2 nt to 6 nt) are directly identified in the Figure. FIG. 1D shows experimental setup for the smFRET analysis of iHabSs using prism-based total internal reflection fluorescence microscopy (pTIRFM). The biotin-modified iHabSs (containing the same or different hairpins depending on the experiments) are immobilized on a biotinylated BSA (bBSA)/streptavidin-coated quartz slide. The Cy3 and Cy5 fluorophores are identified as green and red spheres, respectively.

FIG. 2A are FRET histograms for all iHabSs at 10 mM $Mg^{2+}$. Since the mean FRET value of the open conformation was similar for all iHabSs, the FRET data were combined into a single histogram (gray, negative control). Each histogram at closed conformation is separately plotted and fitted with a single-peak Gaussian function before combining them. The shaded area highlights the unresolved FRET peaks for HP22, HP34, HP45 and HP66 ("unresolved"). FIG. 2B shows FRET analysis of the iHabSs under the same buffer condition as in FIG. 2a except at 2 mM $Mg^{2+}$. The shaded area highlights the resolved FRET peaks ("resolved") that were not resolved at 10 mM $Mg^{2+}$ in FIG. 2a. FIG. 2C shows the mean FRET value for all iHabSs at their closed (circles: 10 mM $Mg^{2+}$, squares: 2 mM $Mg^{2+}$) conformations derived from FIGS. 2A and 2B. The FRET histograms were prepared from 30-220 molecules. The error bars in FIG. 2C represent the standard deviation in the mean FRET values obtained after randomly assigning the molecules of given iHabSs into three groups. Histograms were prepared in Origin for the first 60 frames. HP=hairpin and INT=internal labeling of the Cy3 fluorophore.

FIG. 3A shows bulk FRET analysis showing switching between the low- and high-FRET states of three different iHabSs (HP22, HP66 and INT66) upon alternate addition of the corresponding probe ("P") and target ("T") molecules. Each iHabS is designed to have a unique hairpin-sequence as well as corresponding probes and targets, which are represented in the '(Sx, Px, Tx)' format. Each iHabS was separately analyzed at a 30 nM concentration. 2-fold molar excess of the target or probe was added alternatively to enable the switching. Error bars depict standard deviations (s.d.) from three replicates (n=3). FIG. 3B are fluorescence images of surface-immobilized HP66 (S2, P2, T2) sensor before (top) and after (middle) adding the target. The fluorescence image of the same microscope slide after adding the probe (bottom). Images were from green excitation while red laser was off. FIG. 3C shows smFRET analysis showing switching between a low- and high-FRET state of HP66 by alternate incubation with 1 μM probe and target, respectively. The FRET histograms were prepared from 87-119 molecules. Both the bulk and smFRET analyses were performed in 1×TAE buffer containing 2 mM $Mg^{2+}$ (pH 7.4).

FIG. 4A shows typical intensity-time traces (Cy3: green, Cy5: red) with varying FRET. FIG. 4B (left) shows FRET trajectories corresponding to the typical intensity-time traces on FIG. 4A. FIG. 4B (right) shows an overall FRET histogram. Gray histogram represents the FRET in the absence of target (negative control). Black histogram represents FRET with the addition of 1 μM target. The FRET histograms were prepared from 97-146 molecules. The curves in the histogram depict Gaussian fittings. iHabS assignments depicted in the histograms are post-assignments.

FIG. 5A shows smFRET histograms in the presence of all three targets. FIG. 5B shows method validation by systematically omitting one of the targets in the multiplex assay. Target T3, T2, and T1 was missing on the top, middle, and the bottom panel, respectively. Analyses were performed in 1×TAE buffer containing 2 mM $Mg^{2+}$ and 150 mM NaCl (pH 7.4).

Figure 5A:
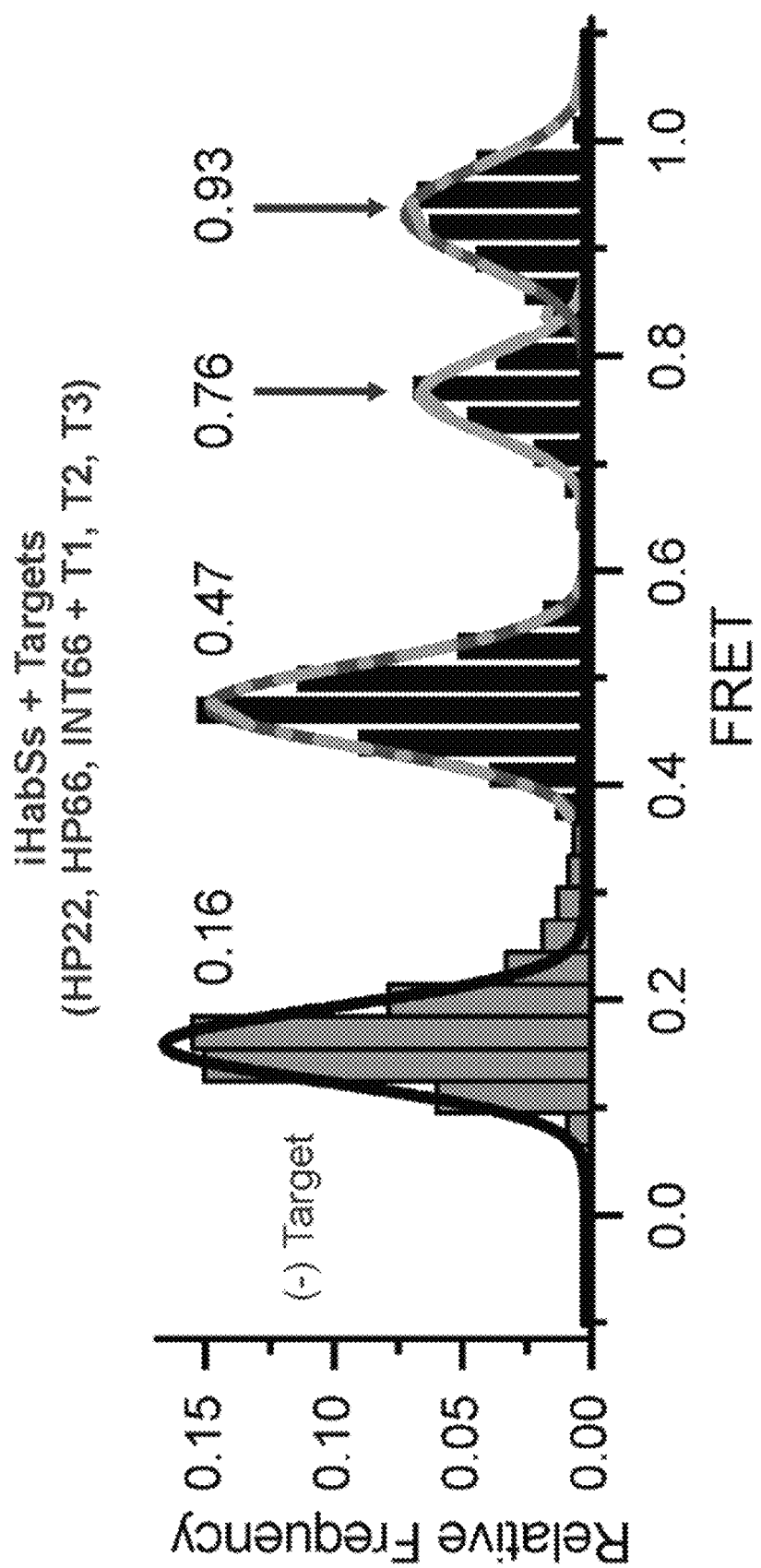
FIGS. 5A and 5B show multiplex detection of DNA.

The FRET histograms were prepared from 43-139 molecules. The grey histogram in (b) is re-used from FIG. 5a for reference.

Figure 6A:
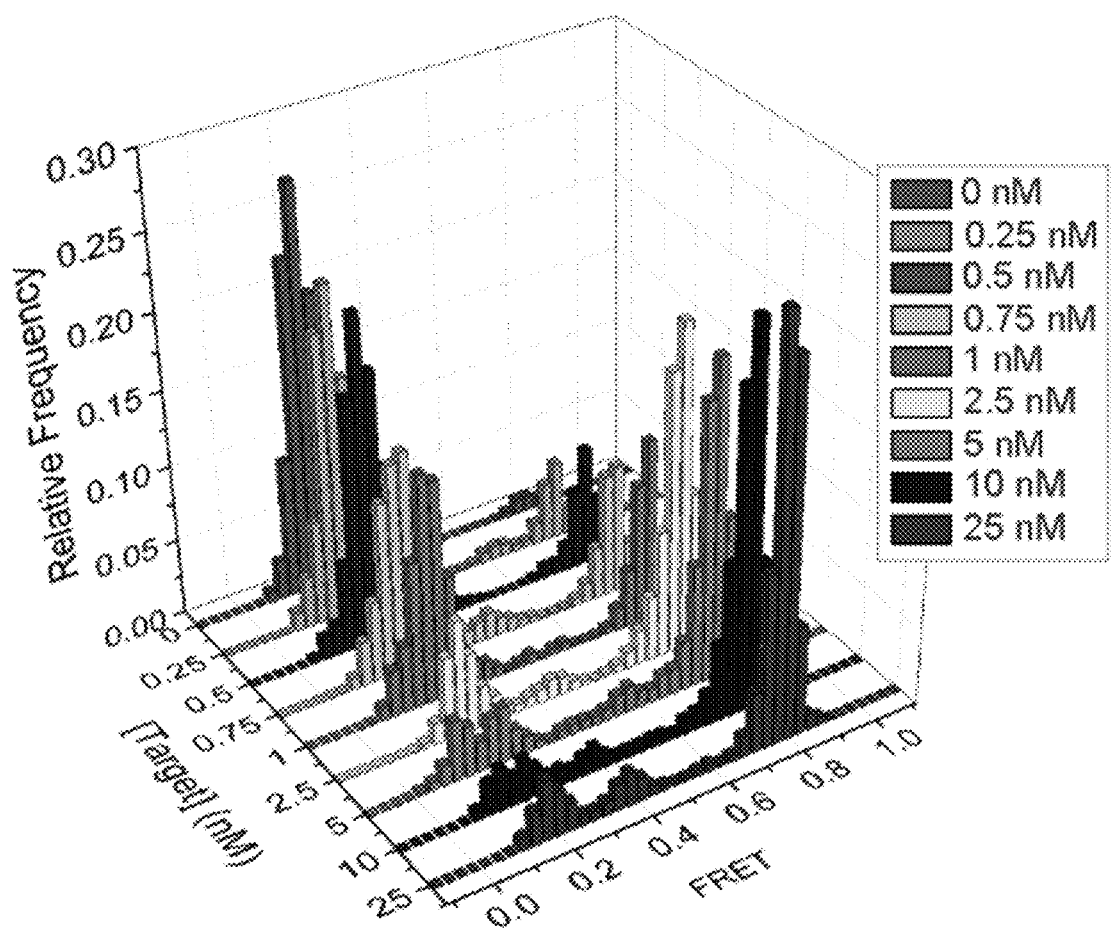
Figure 6B:
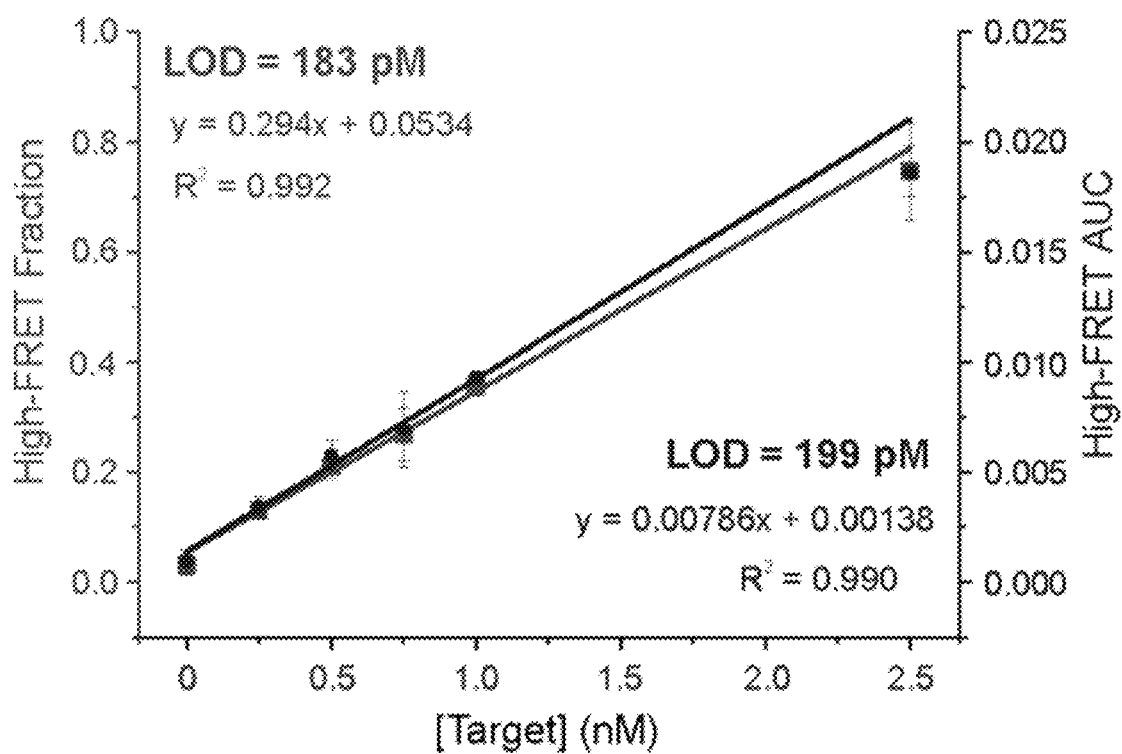

FIGS. 6A and 6B show analytical sensitivity of iHabSs. FIG. 6A are smFRET histograms obtained for different concentrations of targets. One of the iHabSs (HP66) was used in these experiments. FIG. 6B shows standard curve for HP66 (S2, P2, T2). The fraction of high-FRET population determined from the area under the curve (AUC) in FIG. 6A was plotted against [target]. Linear fit yielded $R^2$ value of 0.992 and slope of 0.294. The limit of detection, defined as "(3×s.d.blank)/slope", is 183 pM. The raw high-FRET AUC values were also plotted against [target] showing an $R^2$ value of 0.990, slope of 0.00786, and LOD of 199 pM. Error bars represent the standard deviations (s.d.) (n=3). The FRET histograms were prepared from 90 molecules at each concentration of target.

Figure 7A:
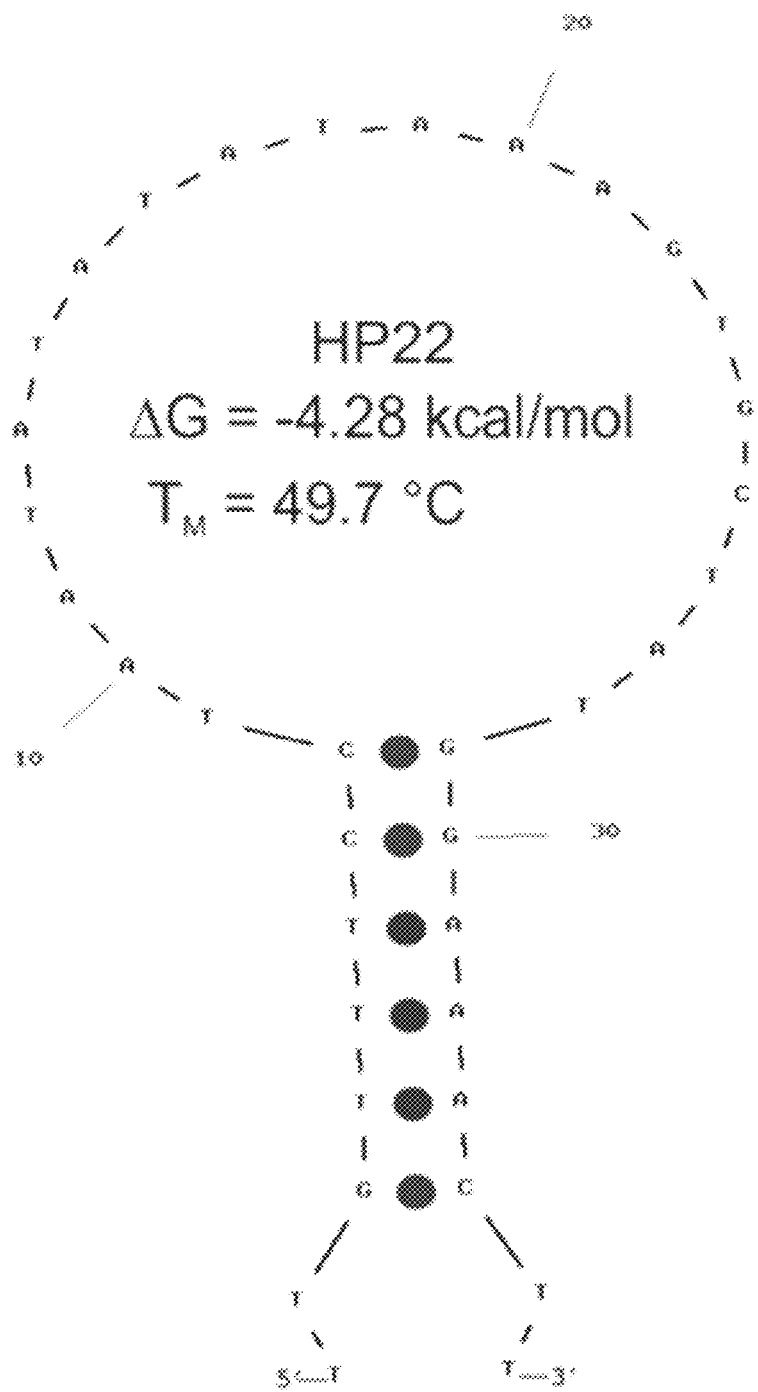
Figure 7B:
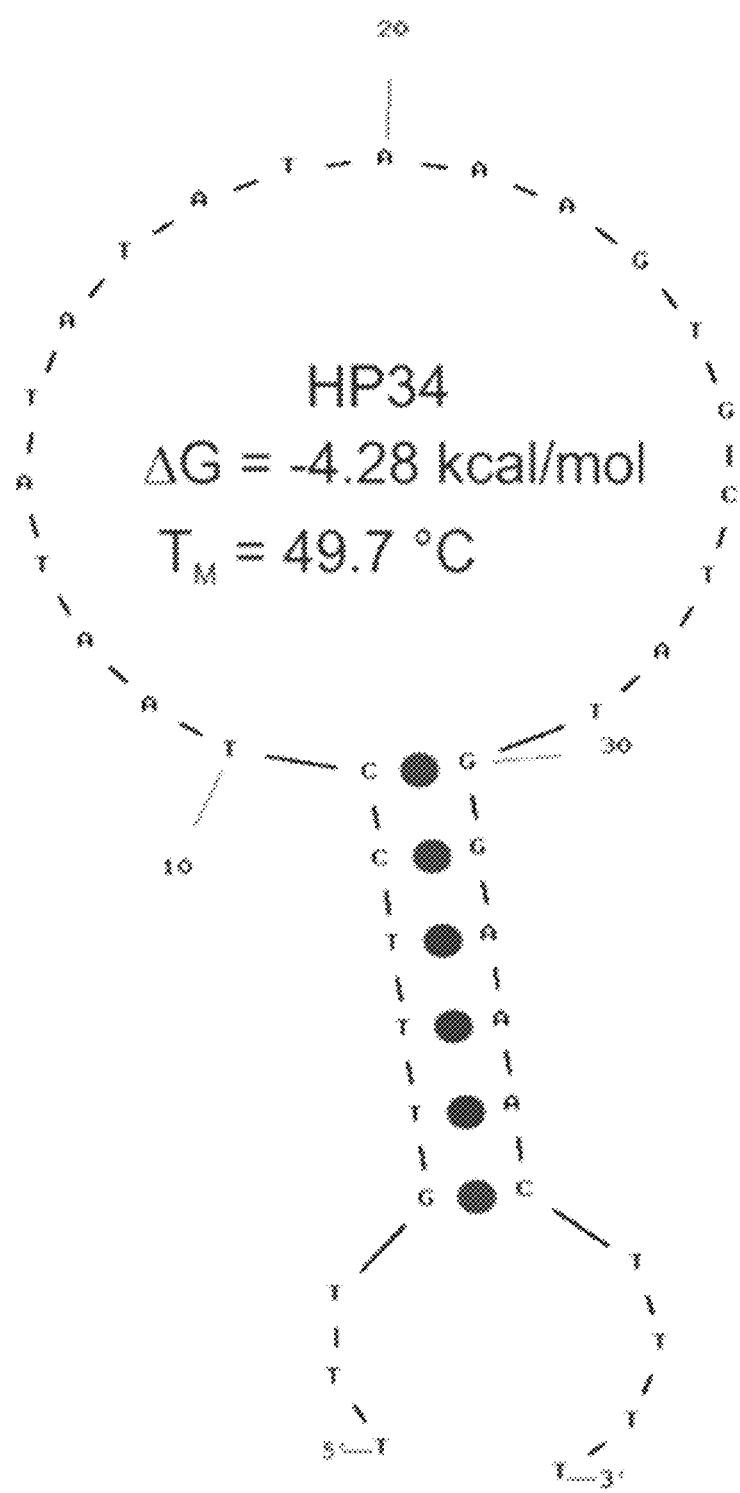
Figure 7C:
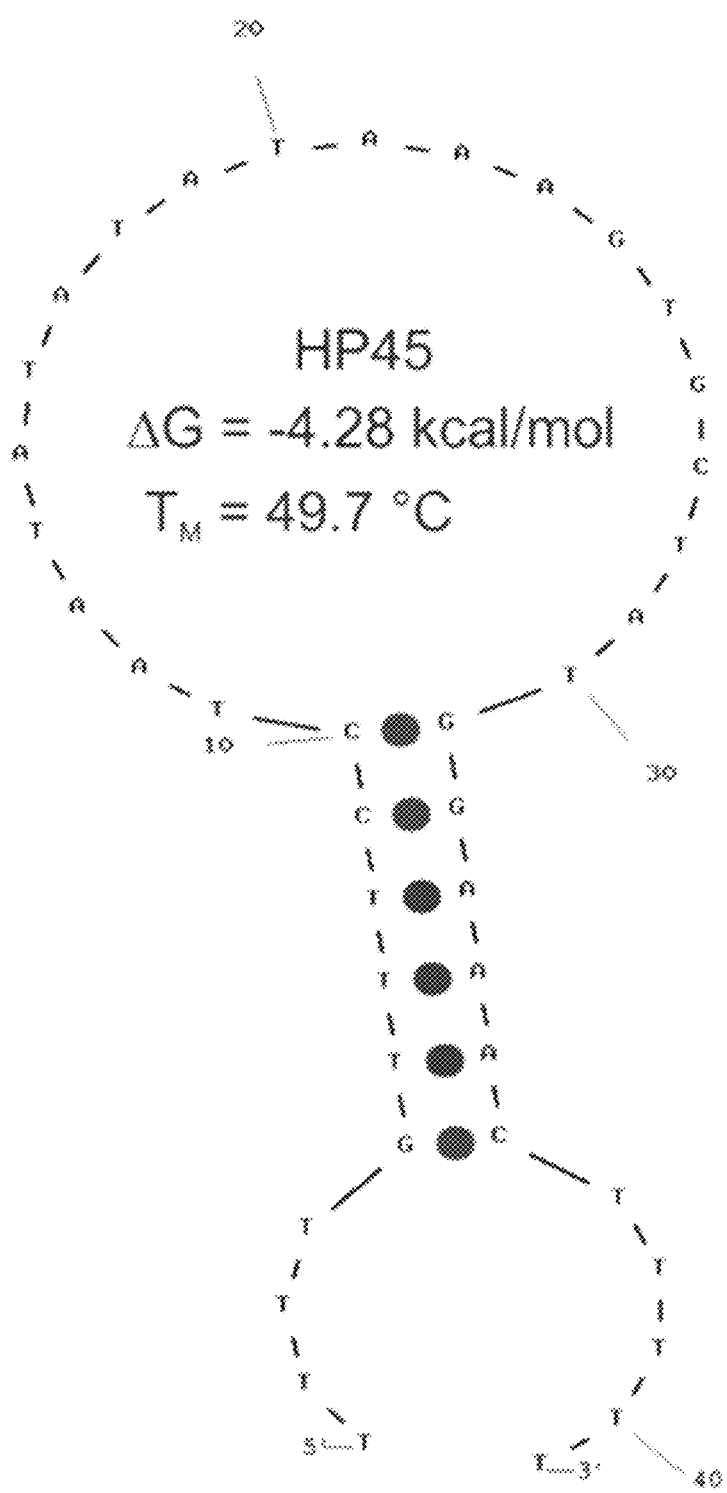
Figure 7D:
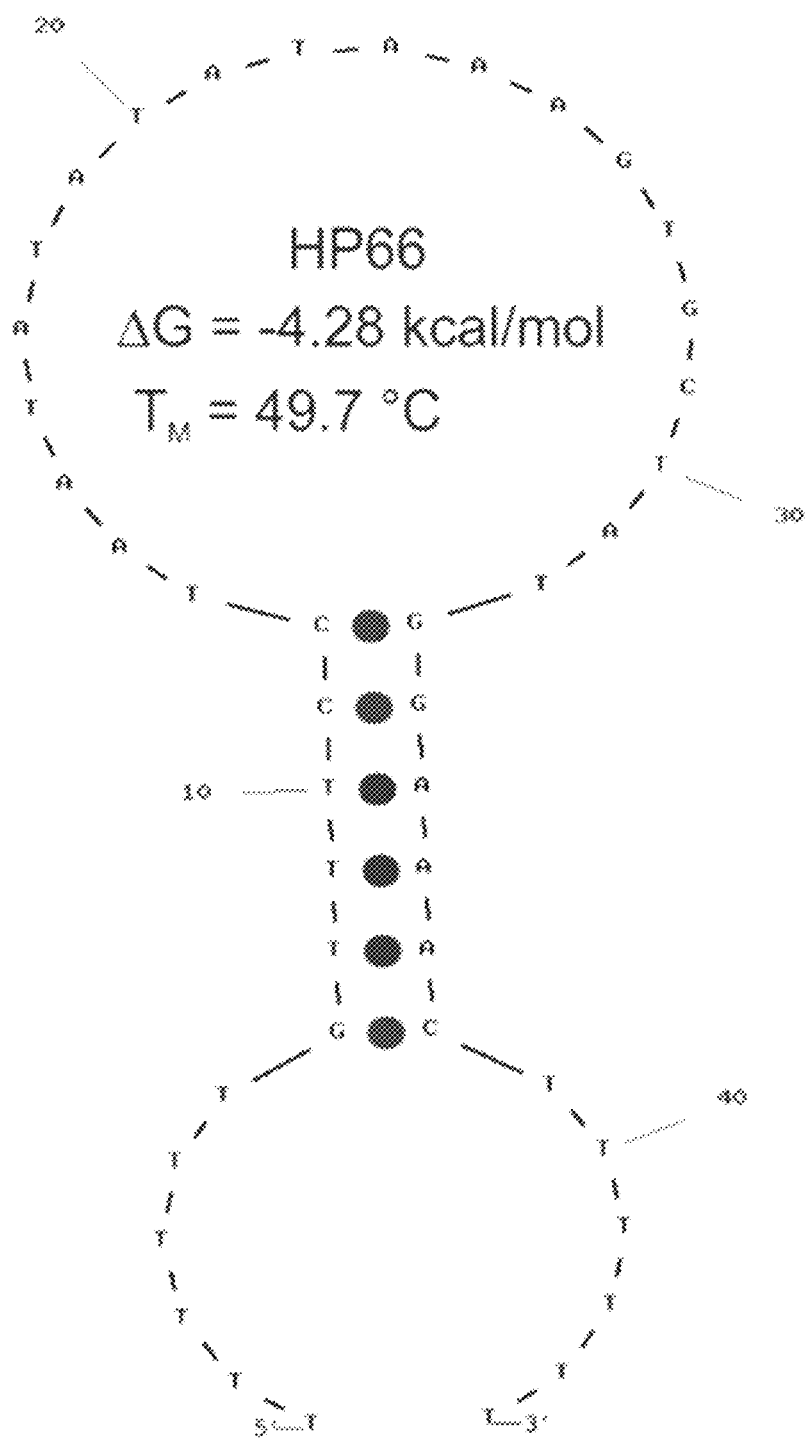

FIGS. 7A to 7D show mFold-predicted structures of DNA hairpins with flanking thymine spacers of various lengths. Included are the ΔG and TM values for DNA hairpins HP22 (FIG. 7A, SEQ ID NO:28), HP34 (FIG. 7B, SEQ ID NO:29), HP45 (FIG. 7C, SEQ ID NO:30), and HP66 (FIG. 7D, SEQ ID NO:31). Structures predicted by the Integrated DNA Technologies (IDT) UNAFold tool in the presence of 2 mM $Mg^{2+}$. All of the hairpins exhibit the same thermal stability as indicated by the same ΔG and TM values.

Figure 8:
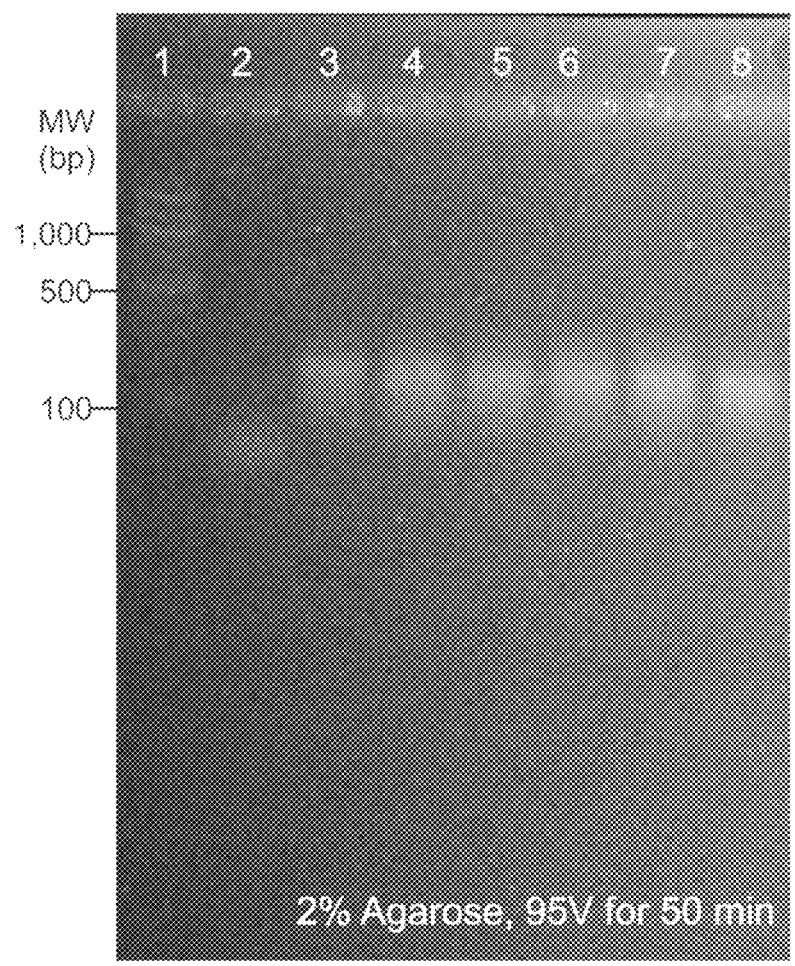

FIG. 8 is a 2% Native agarose gel showing the formation of iHabSs run for 45 min at 95 V in the presence of 12.5 mM $Mg^{2+}$. All iHabSs were assembled at their open conformation in the presence of probes. All iHabSs (lanes 3-8) show a slower migration compared to the ssDNA reference (lane 2), confirming the formation of desired constructs. Lane 1: DNA molecular weight (MVV) marker, lane 2: 40-nucleotide ssDNA, lane 3: HP22, lane 4: HP34, lane 5: HP45, lane 6: HP66, lane 7: INT66, lane 8: INT34.

Figure 9:
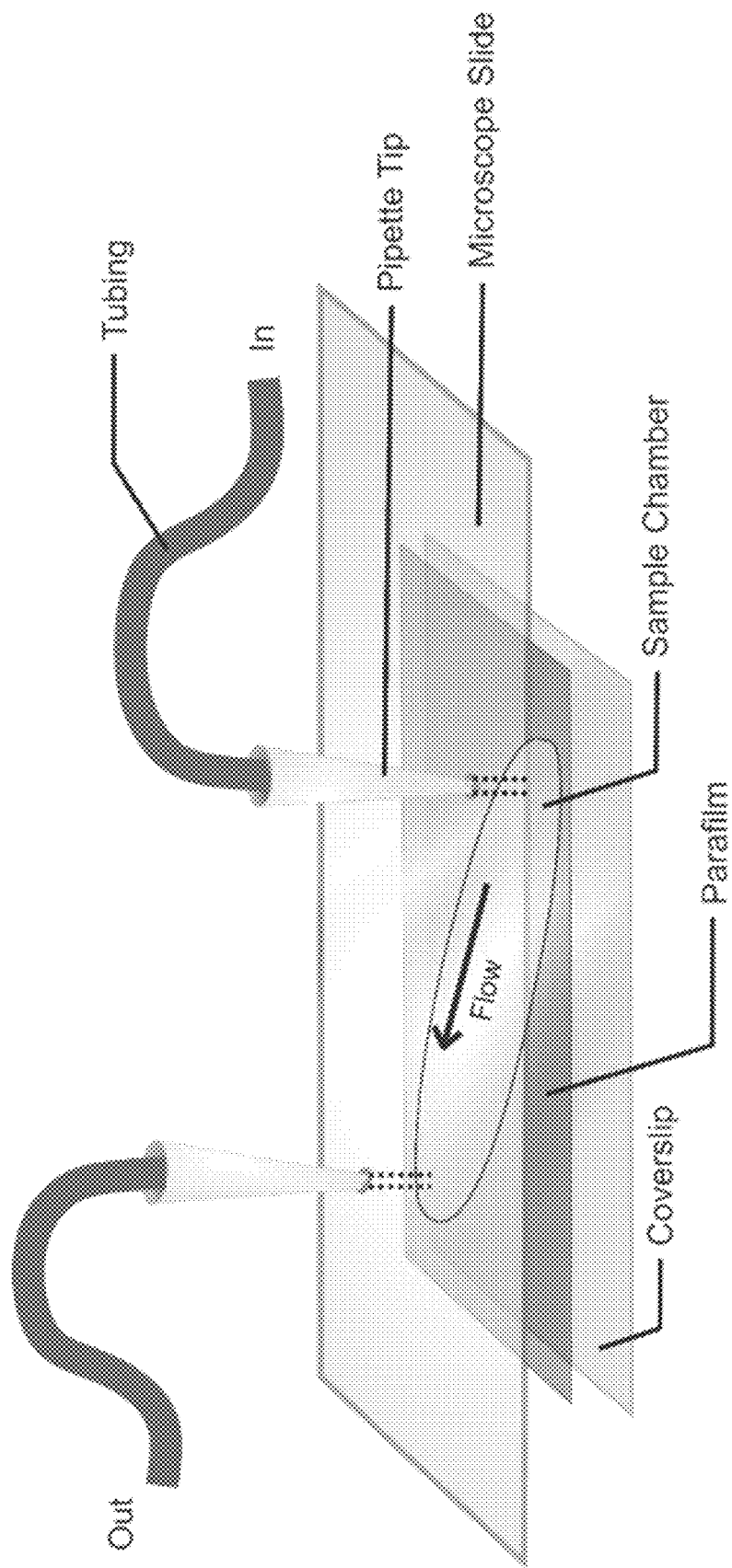

FIG. 9 is a schematic of a pTIRF flow cell. Parafilm with a precut sample chamber large enough to contain the drilled holes of the microscope slide is sandwiched between a glass coverslip and a quartz slide. Pipette tips and tubing are inserted to complete the flow cell. Layers are separated for easy visualization of flow cell components.

Figure 10B:
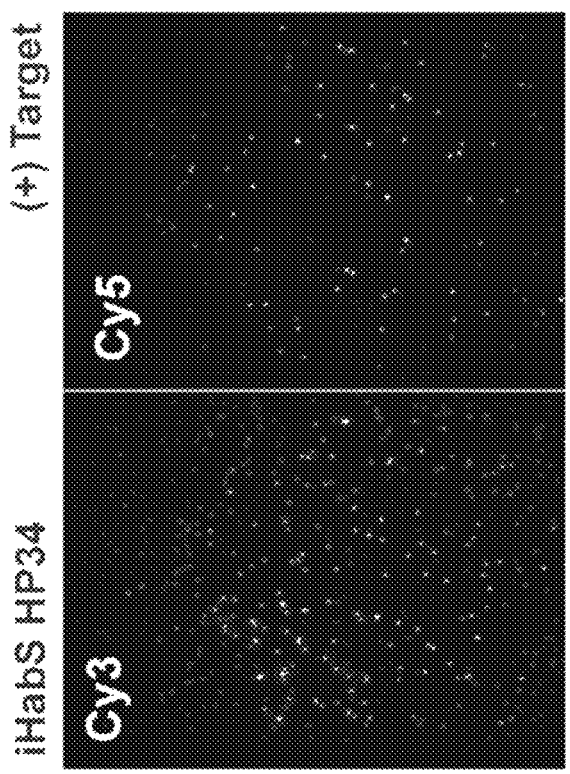
Figure 10A:
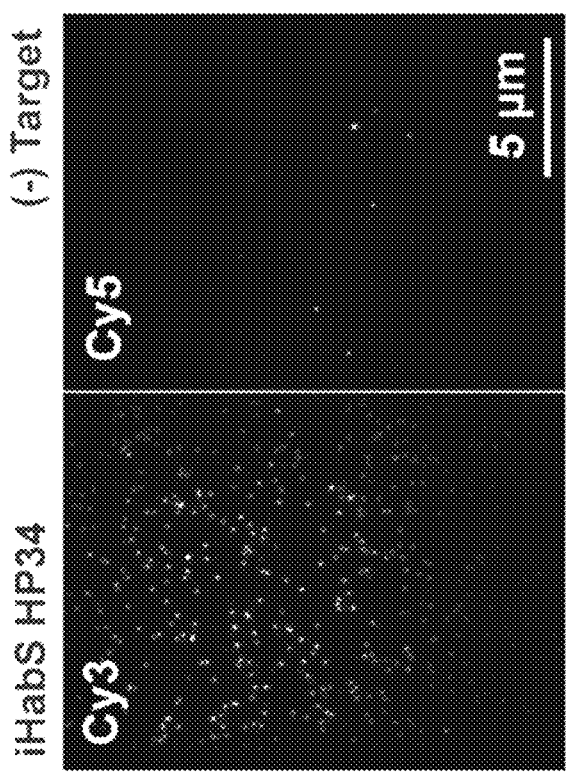

FIGS. 10A and 10B show typical smFRET field of view for an iHabS immobilized on a quartz slide both with (FIG. 10A) and without (FIG. 10B) target. Representative fields of view shown are for iHabS HP34 (S3, P3, T3). Images were taken under green (532 nm) illumination. Left channels show fluorescence emission of Cy3 and right channels show emission of Cy5.

Figure 11A:
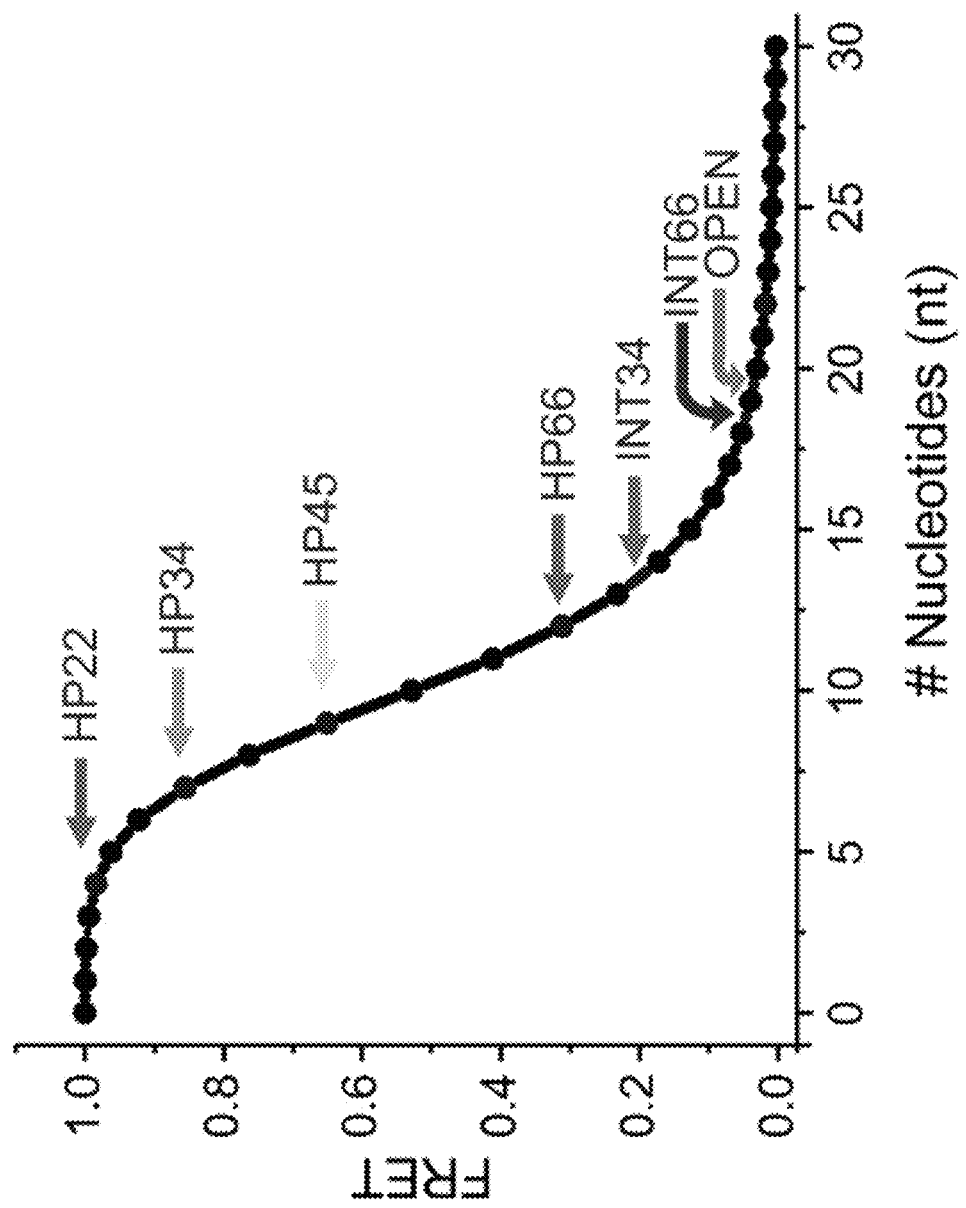
Figure 11B:
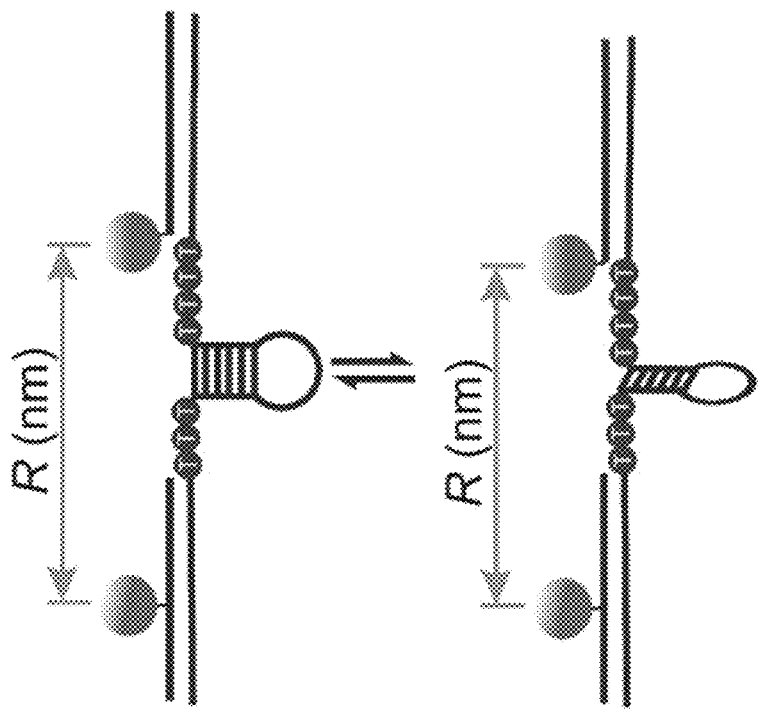

FIG. 11A is a plot of calculated FRET vs. the number of nucleotide (nt) spacers, where the iHabS tested are indicated with arrows. FRET was calculated using the equation:

$$FRET\ \text{Efficiency} = \frac{1}{1 + \left(\frac{R}{R_0}\right)^6},$$

where R is the inter-dye distance between two fluorophores and R0 is the inter-dye distance at which the FRET is equal to 0.5 (5.4 nm for the Cy3 and Cy5 donor/acceptor pair). Arrows point to where each iHabSs and the open conformation lie on the plot. FIG. 11B is an estimation of the inter-dye distance R for a typical iHabS calculated assuming a completely linear structure. An average of 1 nm length is assumed for distance added by the hairpin stem considering the fact that the maximum dimension of the hairpin stem is 2 nm but the hairpin can fluctuate between different conformational orientations relative to the spacers. Distance of the spacers is calculated assuming the average single-nucleotide contour length to be 0.43 nm. Thus the equation used is R=(#nt*0.43)+1. In the case of internal labeling (INT), Cy3 is labeled 8 nt from the terminal position and thus the dsDNA portion containing 8 base pairs (bp) is added to the calculation as follows: R=(#nt*0.43)+(8*0.34)+1, where 0.34 is the base-pair (bp) contour length of dsDNA.

Figure 12A:
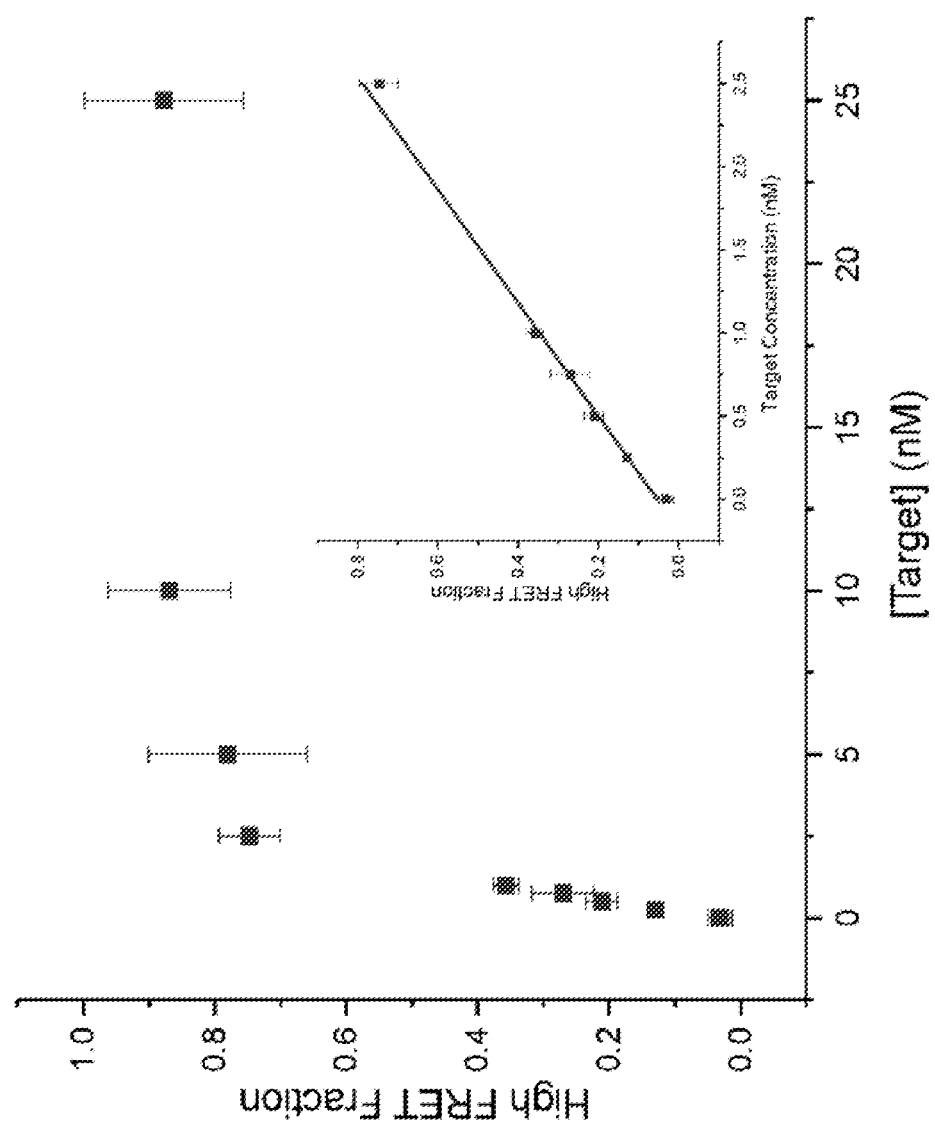
Figure 12B:
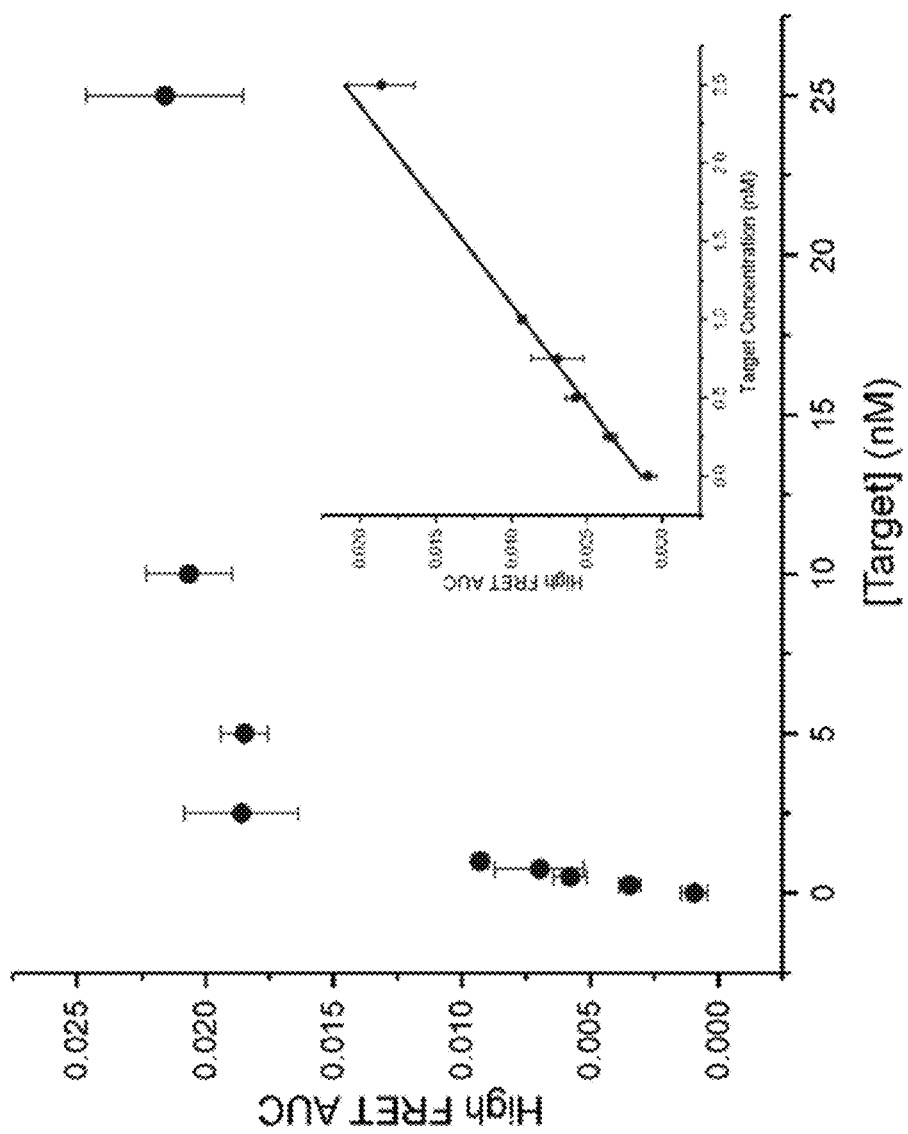

FIGS. 12A and 12B are standard curves for iHabS HP66 (S2). FIG. 12A is a full standard curve plotting the high FRET Fraction against the target concentration. Inset depicts the linear region of the curve with a linear fit. The high FRET population is determined from the area under the curve (AUC) of the multi-peak Gaussian fitting of the histograms shown in FIG. 6 and dividing the area of the high FRET population by the sum of the area of the low- and high-FRET populations for each histogram of each target concentration tested as seen in the following equation:

$$\text{High } FRET \text{ Fraction} = \frac{\text{High } FRET \text{ AUC}}{(\text{High } FRET \text{ AUC} + \text{Low } FRET \text{ AUC})}$$

Error bars represent the standard deviations in the mean FRET values obtained by assigning the molecules of a given target concentration into three groups (n=3). As seen in FIG. 6 there is a linear range up to 2.5 nM after which the data begins to plateau suggesting saturation of the iHabS sensor. FIG. 12B is a full curve plotting the raw AUC values for the high FRET population against target concentration. Inset depicts linear region of the curve with linear fit.

Figure 13A:
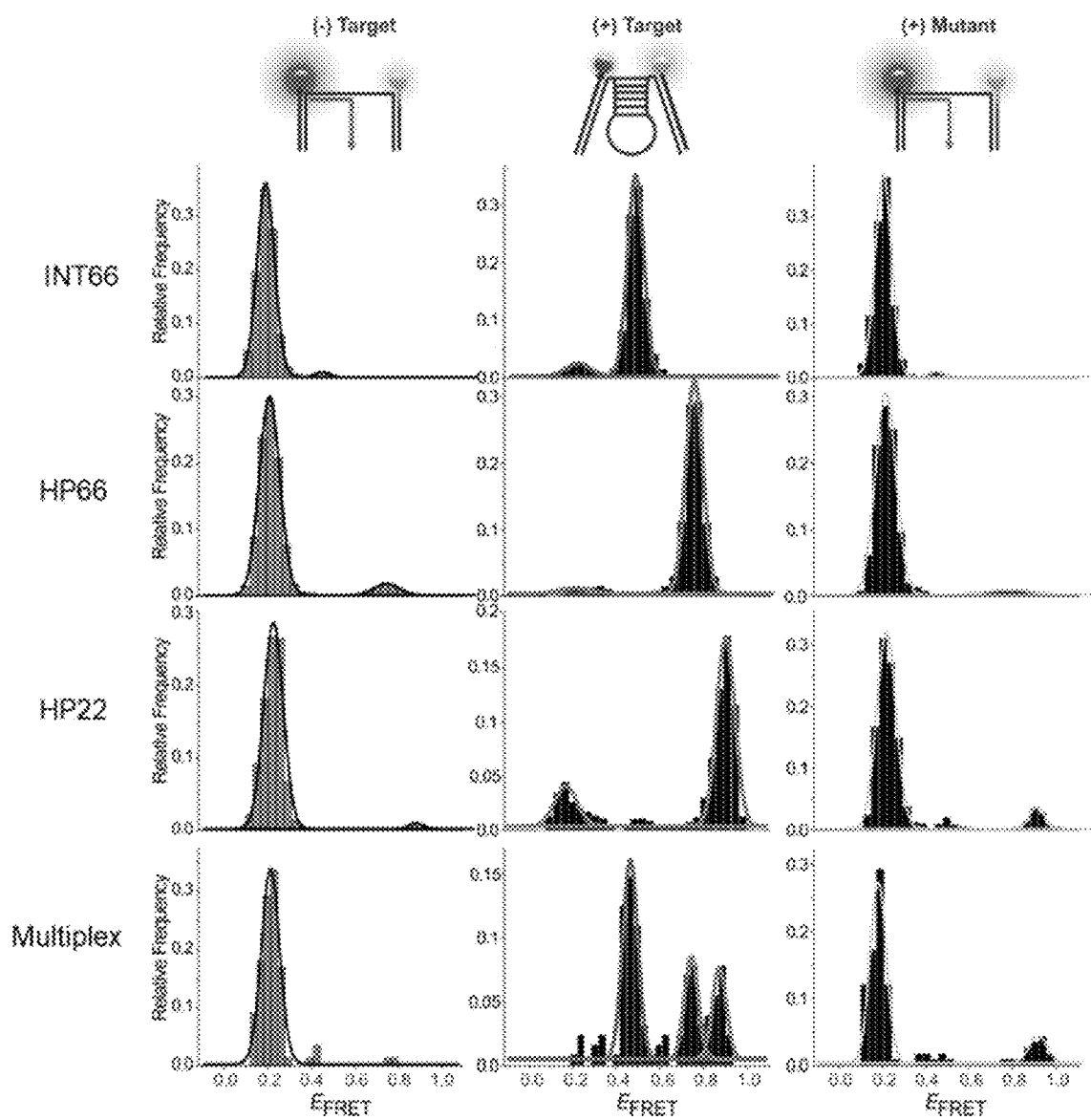
Figure 13B:
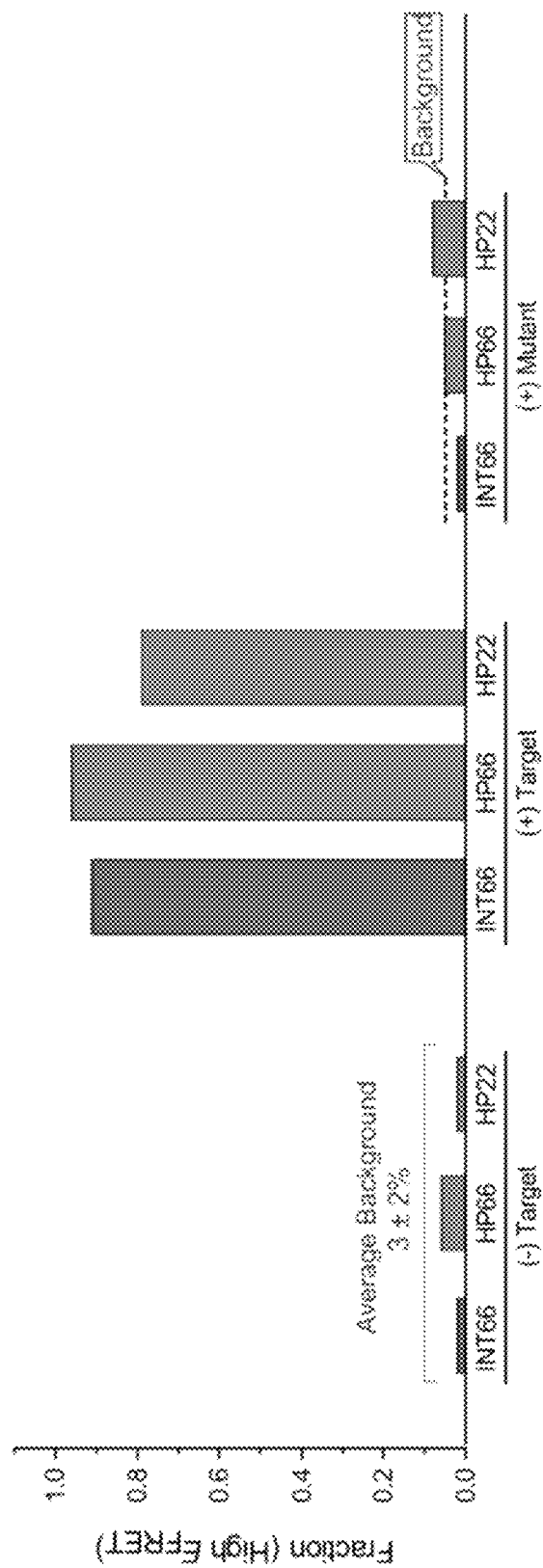

FIGS. 13A and 13B show specificity of iHabSs. FIG. 13A shows specificity of the iHabSs analyzed in the presence of either the target or the mutant. The sequences of probes, targets, and mutants for different iHabSs are as follows:

```
GTGGCTGCTTTTCAACTGTTG  (INT66 Probe, SEQ ID NO: 19),

CAACAgTTGAAAAGCAGCCAC  (INT66 Target, SEQ ID NO: 20),

CAACAaTTGAAAAGCAGCCAC  (INT66 mutant, SEQ ID NO: 21),

AGCACTGTAGTTGAAGATGGT  (HP66 probe, SEQ ID NO: 22),

ACCATcTTCAACTACAGTGCT  (HP66 Target, SEQ ID NO: 23),

ACCATtTTCAACTACAGTGCT  (HP66 mutant, SEQ ID NO: 24),

TTTCCATAGCACTTTTTACAT  (HP22 probe, SEQ ID NO: 25),

ATGTAaAAAGTGCTATGGAAA  (HP22 target, SEQ ID NO: 26),

ATGTAgAAAGTGCTATGGAAA  (HP22 mutant, SEQ ID NO: 27).
```

The toehold regions are bolded and the mutations are lower case. The smFRET histograms of individual sensors in the absence (left panel) and presence (middle panel) of their corresponding fully complementary targets or in the presence of mutant targets (right panel) at 5 nM are shown. The FRET efficiency histograms were prepared from 77-146 molecules. Similarly, the bottom panel shows the smFRET histograms for the simultaneous imaging of three iHabSs in the absence (left panel) and presence (middle panel) of all three targets as well as in the presence of all three mutants (right panel), each added at a concentration of 5 nM. Histograms for the multiplexed assays were prepared from 102-120 molecules by binning the mean FRET efficiency for each molecule. FIG. 13B is a comparison of the high-EFRET fraction among various iHabSs in the absence and presence of fully complementary and in the presence of single-base mismatch targets. The horizontal dotted line represents the average background of these iHabSs determined from the experiments in FIG. 13A.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 23° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Interconvertible Hairpin-Based Sensors (iHabSs)

Figure 1A:
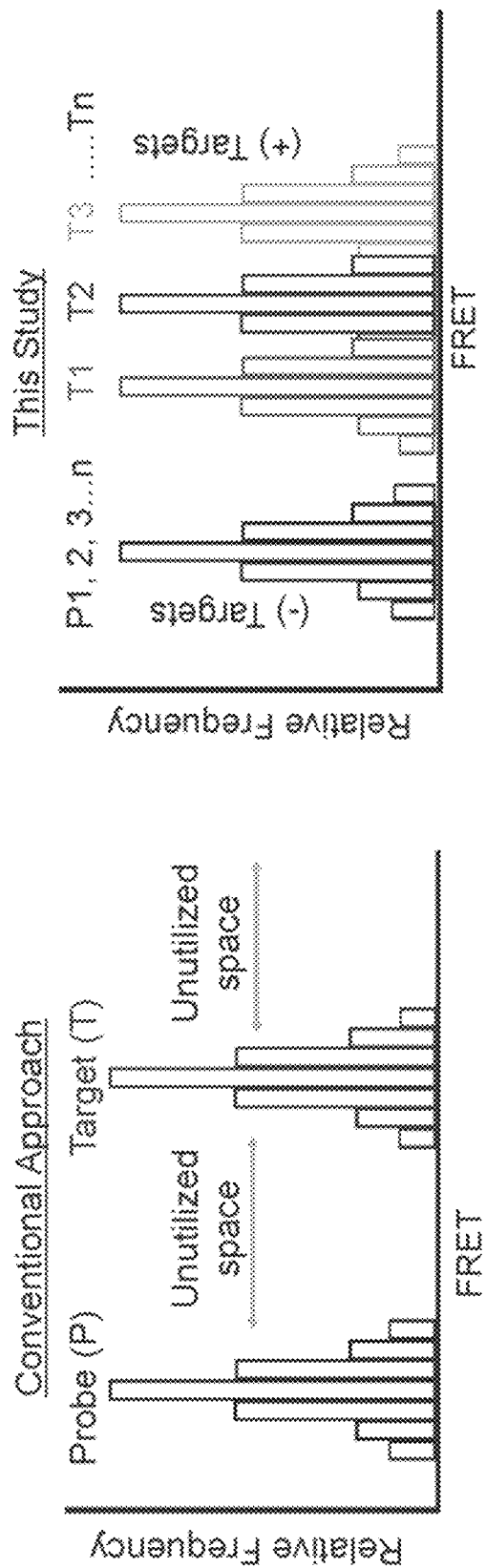
FIGS. 1A to 1D show experimental design and single-molecule characterization of interconvertible hairpin-based sensors (iHabSs).
Figures 1B, 1C:
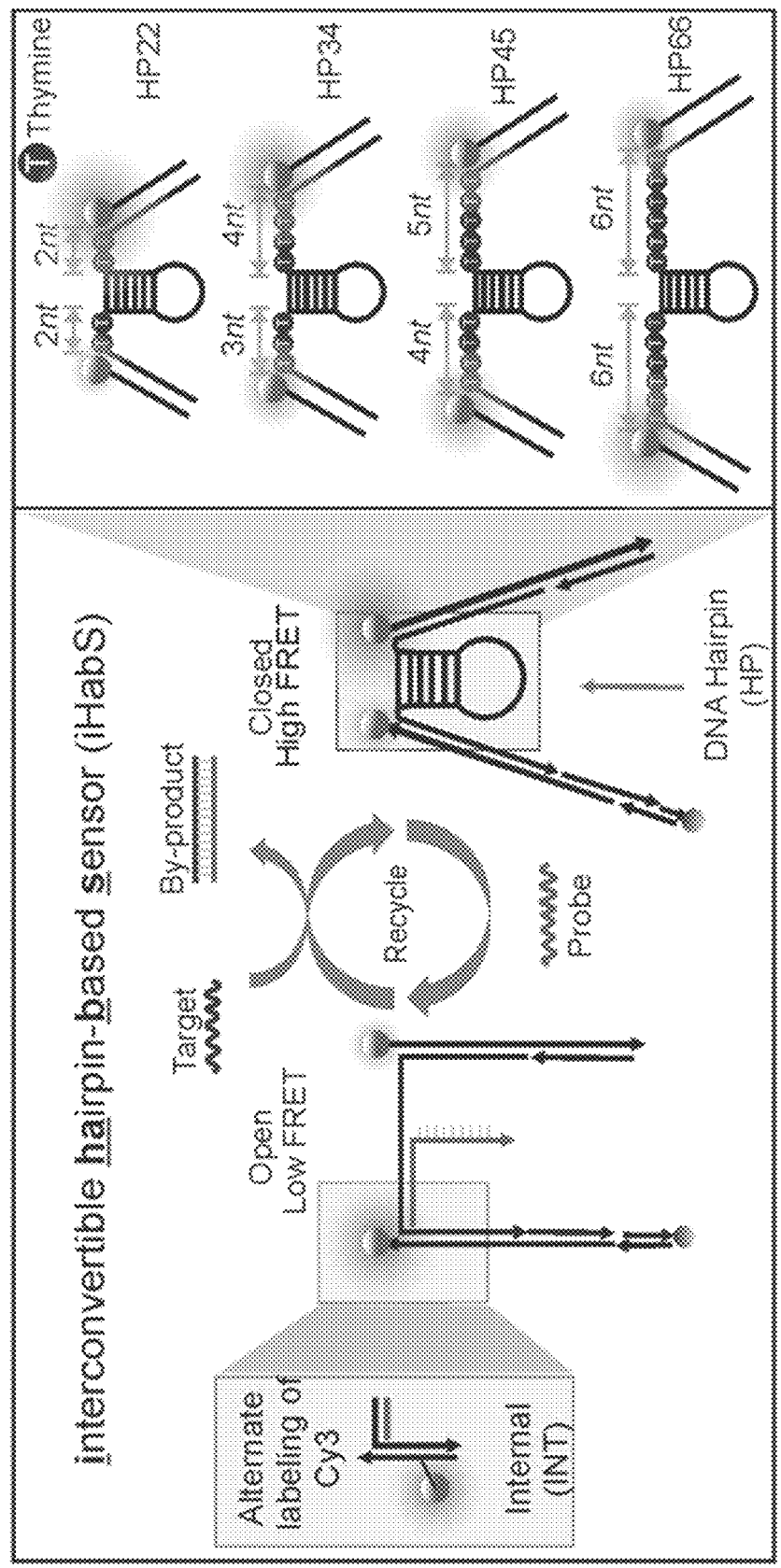

Disclosed herein is an approach for multiplex detection of biomolecules by rational designing of DNA-based smFRET sensors, referred to herein as interconvertible hairpin-based sensors (iHabSs), which allow multiplex detection by filling the FRET gaps (FIG. 1A). iHabS involves two short pieces of double-stranded DNA each labeled with a donor or acceptor fluorophore which sandwich a DNA-hairpin that is flanked on both sides by thymine spacers (FIGS. 1B and 1C). The unique design of the hairpin allows hybridization of a DNA probe to a portion of the hairpin and toehold-mediated displacement of the probe by the target thus enabling detection by increase in FRET (FIG. 1B). Multiplexing is achieved using a combination of iHabSs with unique inter-dye distances tuned by the length of flanking thymine-spacers (FIG. 10). For example, simultaneous detection of three different targets (DNA sequences) can be achieved, producing three spectrally resolvable FRET signals. With fine tuning of the spacer lengths and utilizing both sides of the hairpins to recruit probes, these iHabSs have the potential for the detection of at least six targets. Additionally, these sensors exhibit many desirable features, for example they are fully-recyclable via the alternate addition of probe and target sequences (simple one-step conversion) for multiple rounds of detection and are highly sensitive with a detection limit down to a low picomolar (pM) concentration. Further, unlike expensive enzymes or antibody-based sensors, iHabSs can be readily prepared from short synthetic DNA strands. With such a multitude of features, the multiplexed method developed here is directly applicable in biotechnology and diagnostics for a simple, accurate, and inexpensive analysis of unlabeled nucleic acids biomarkers such as circulating microRNAs (Mo, M.-H., et al. (2012) J Cancer 3:432-448; Iorio, M. V., et al. (2012) EMBO Mol Med. 4:143-159).

"Single-molecule fluorescence resonance energy transfer" (or "smFRET") is the application of FRET techniques to study a single molecule with at least two fluorescent labels, or the interaction of at least two molecules, each with a label. Fluorescence Resonance Energy Transfer (FRET) is a non-radiative pathway by which a molecule in an electronic excited state may relax back to the more stable ground state. The transfer of energy occurs through space via dipole-dipole interaction: energy from the excited-state molecule (the donor fluorophore) may transfer to a neighboring molecule (the acceptor fluorophore) given significant degree of spectral overlap between donor emission and acceptor absorption, properly oriented dipole moments of the interacting dye molecules, and the appropriate distance between the two fluorophores. In smFRET the donor and receptor fluorophores are either on the same molecule, or are on different molecules that interact, bringing the two fluorophores into proximity. The detection of FRET at the single-molecule scale enables the direct measurement of conformational events on biologically-relevant time scales. At least two fluorophores are required.

The donor fluorophore will be under direct excitation by a laser. When the donor is brought within close proximity to the acceptor, energy is transferred from the donor to the acceptor at an efficiency that is dependent on the inter-dye distance. This efficiency is described by the relationship $FRET=1/(1+(R/R_0)^6)$, where R is the inter-dye distance, and $R_0$ is the Förster distance at 50% FRET efficiency, which determines the scale on which FRET is a sensitive measure of distance. The commonly used cyanine dyes (Cy3 and Cy5) have an $R_0$ of ~54 Å and a response range of ~30-80 Å. From fluorescence trajectories, the FRET efficiency (or the FRET value) can be calculated according to $FRET=I_A/(I_A+I_D)$, where $I_A$ is the intensity of acceptor fluorescence, and $I_D$ is that of the donor.

A "fluorophore" is a chemical compound or a component of a molecule which causes a molecule to be fluorescent. It is a molecule or a functional group (in some cases) in a molecule which will absorb energy of a specific wavelength and re-emit energy at a specific wavelength. The amount and wavelength of the emitted energy depend on both the fluorophore and the chemical environment of the fluorophore. In some embodiments, fluorophores from the cyanine family are used in the method disclosed herein. The cyanine dyes, Cy3 and Cy5 are well-established for use in smFRET imaging owing to their brightness, photostability, and water solubility. Derivates of cyanine fluorophores with further improved photostability have also been developed and can be used in the disclosed composition and methods.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Results

Design, Assembly, and Characterization of Sensors

In this study, a simple, sensitive, and fully-recyclable FRET-based multiplex detection platform was designed to overcome current requirements of complex labeling schemes and complicated data analysis algorithms and employ smFRET microscopy in multiplexing. While conventional smFRET detection techniques allow for the analysis of one target at a time, the disclosed approach utilizes the gaps between high and low FRET histograms (FIG. 1A) to allow simultaneous detection of multiple targets. For this, a combination of DNA hairpins were used with various lengths of flanking single-stranded sequences were are designed to be interconvertible between the open and closed conformations to enable detection via FRET change. The sequence design, construction, and working principle of the disclosed "iHabSs" are shown in FIG. 1B. All iHabSs were prepared by thermal annealing of eight single-stranded DNA (ssDNA) oligonucleotides (Table 1) in 1×TAE-Mg buffer (40 mM Tris, 20 mM acetic acid, 1 mM EDTA, 12.5 mM $Mg^{2+}$, pH 7.4). The thermal annealing was carried out by ramping the temperature of the solution from 95° C. to 4° C. in a thermal cycler (Table 2) for a period of 2 hr. The hairpin in all iHabSs is comprised of a 6 base pair (bp)-stem and a 20 nucleotide loop (see FIG. 7 for mFold-predicted structures). The assembly was confirmed by a slower migration of iHabSs compared to an ssDNA control in a 2% native agarose gel (FIG. 8). To allow detection of targets by monitoring the FRET in the absence and presence of targets, the donor (Cy3) and acceptor (Cy5) fluorophores were incorporated into the constructs using fluorophore-labeled complementary oligos (FIG. 1B). This was achieved by designing probes that are complementary to a portion of the hairpin sequences so that a low-FRET is maintained in the absence of targets. However, in the presence of targets, the probes are removed from the iHabSs by toehold-mediated displacement, leading to the formation of hairpins thereby switching the iHabSs from the low- to high-FRET states (detection). While all of the iHabSs share a common low-FRET state, to achieve an iHabS-specific high-FRET in multiplex detection, the hairpins were designed to have flanking thymine spacers of various lengths (represented as the number of thymine nucleotides "nt", FIG. 1C).

TABLE 1

Sequences for all the DNA oligonucleotides used in assembling iHabSs.

| Strand Name | Sequence (5'-3') |
|---|---|
| Cy3-Rdm1 | TCTTGTGAACTCCCTACTATCCTTAAACGCATATCTCTGA/Cy3/ (SEQ ID NO: 1) |
| Cy5-Rdm2 | /Cy5/GTGTATGACCCCTATATGTGAGCTTCTGATGTTACCCGAG (SEQ ID NO: 2) |
| Strand 1 | ATAGTAGGGAGTTCACAAGATGTATAAGCAAATATTTAAA (SEQ ID NO: 3) |
| Bio5'Comp | TTGCATGCCTGCAGGTCGACTCTAGTTTTT/Bio-3'/ (SEQ ID NO: 4) |
| Cy5-Rdm2 Comp bottom | CTCGGGTAACATCAGAAGCT (SEQ ID NO: 5) |
| BioStrand1 Comp | TCAGAAGCTCTCATATAGAGGTCATACACTAATCGAGTAGTGAGTTC (SEQ ID NO: 6) |
| HP22 (S3) | CACATATAGGGGTCATACACTTGTTTCCTAATATATAAAGTGCTATGGAAACTTTCAGAGATATGCGTTTAAGG (SEQ ID NO: 7) |
| HP34 (S3) | CACATATAGGGGTCATACACTTTGTTTCCTAATATATAAAGTGCTATGGAAACTTTTTCAGAGATATGCGTTTAAGG (SEQ ID NO: 8) |
| HP45 (S3) | CACATATAGGGGTCATACACTTTTGTTTCCTAATATATATAAAGTGCTATGGAAACTTTTTCAGAGATATGCGTTTAAGG (SEQ ID NO: 9) |
| HP66 (S3) | CACATATAGGGGTCATACACTTTTTGTTTCCTAATATATATAAAGTGCTATGGAAACTTTTTTCAGAGATATGCGTTTAAGG (SEQ ID NO: 10) |
| P3 | TTTCCATAGCACTTTTTACATACCT (SEQ ID NO: 11) |
| T3 | AGGTATGTAAAAAGTGCTATGGAAA (SEQ ID NO: 12) |
| HP66 (S2) | CACATATAGGGGTCATACACTTTTTTAGCACTAATATATATTTCAACTACAGTGCTTTTTTTTCAGAGATATGCGTTAAGG (SEQ ID NO: 13) |

TABLE 1-continued

Sequences for all the DNA oligonucleotides used in assembling iHabSs.

| Strand Name | Sequence (5'-3') |
|---|---|
| P2 | AGCACTGTAGTTGAAGATGGTTCAC (SEQ ID NO: 14) |
| T2 | GTGAACCATCTTCAACTACAGTGCT (SEQ ID NO: 15) |
| INT66 (S1) | CACATATAGGGGTCATACACTTTTTTGGTGGTAATATATATTTGAAAAGCAGCCACCTTTTTTTCAGAGATATGCGTTTAAGG (SEQ ID NO: 16) |
| P1 | AGCACTGTAGTTGAAGATGGTTCAC (SEQ ID NO: 17) |
| T1 | GTGAACCATCTTCAACTACAGTGCT (SEQ ID NO: 18) |

All biotin- and fluorophore-modified DNA oligos were purchased HPLC purified. Sx, Px, and Tx refer to the specific DNA sequences, probes, and targets respectively, where x represents 1, 2, or 3. Rdm = random sequence, bio = biotin labeled, comp = complementary, INT = internal labeling of Cy3.

TABLE 2

Thermal annealing program for the assembly of iHabSs.

| Temperature (° C.) | Time (min) |
|---|---|
| 95 | 5 |
| 93 | 5 |
| 90 | 5 |
| 88 | 5 |
| 86 | 5 |
| 84 | 5 |
| 82 | 5 |
| 80 | 5 |
| 78 | 5 |
| 76 | 5 |
| 72 | 5 |
| 68 | 5 |
| 64 | 5 |
| 60 | 5 |
| 56 | 5 |
| 52 | 5 |
| 48 | 5 |
| 44 | 5 |
| 40 | 5 |
| 36 | 5 |
| 32 | 5 |
| 28 | 5 |
| 24 | 5 |
| 4 | hold |

First, the performance of the iHabSs was determined by smFRET experiments on a prism-based TIRF (pTIRF) microscope (Gibbs, D. R., et al. (2018) Biochemistry 57:3616-3624). Briefly, one of the oligos in each iHabS was biotin-modified (Table 1) to enable surface-immobilization on the microscope slide which is coated with biotin-BSA and streptavidin (see Methods). The design of the flow cell is shown in FIG. 9. Upon binding of the iHabS(s), the unbound molecules were washed off with an imaging buffer (1×TAE-Mg, pH 7.4) containing an oxygen-scavenging system (OSS) (Aitken, C. E., et al. (2008) Biophysical Journal 94:1826-1835; Fu, J., et al. (2016) Nature Protocols 11:2243). The OSS helps to retard photobleaching of the fluorophores upon laser-illumination. The fluorescence intensity traces were recorded at 10 frames per second (≈100 ms camera integration time) for both Cy3 and Cy5 while the microscope slide was illuminated only with the green laser (532 nm). The presence of fully assembled iHabSs were confirmed by direct excitation of Cy5 (red laser, 639 nm) towards the end of data acquisition. Only the molecules containing both Cy3 and Cy5 were picked manually for further FRET analysis.

Figure 1D:
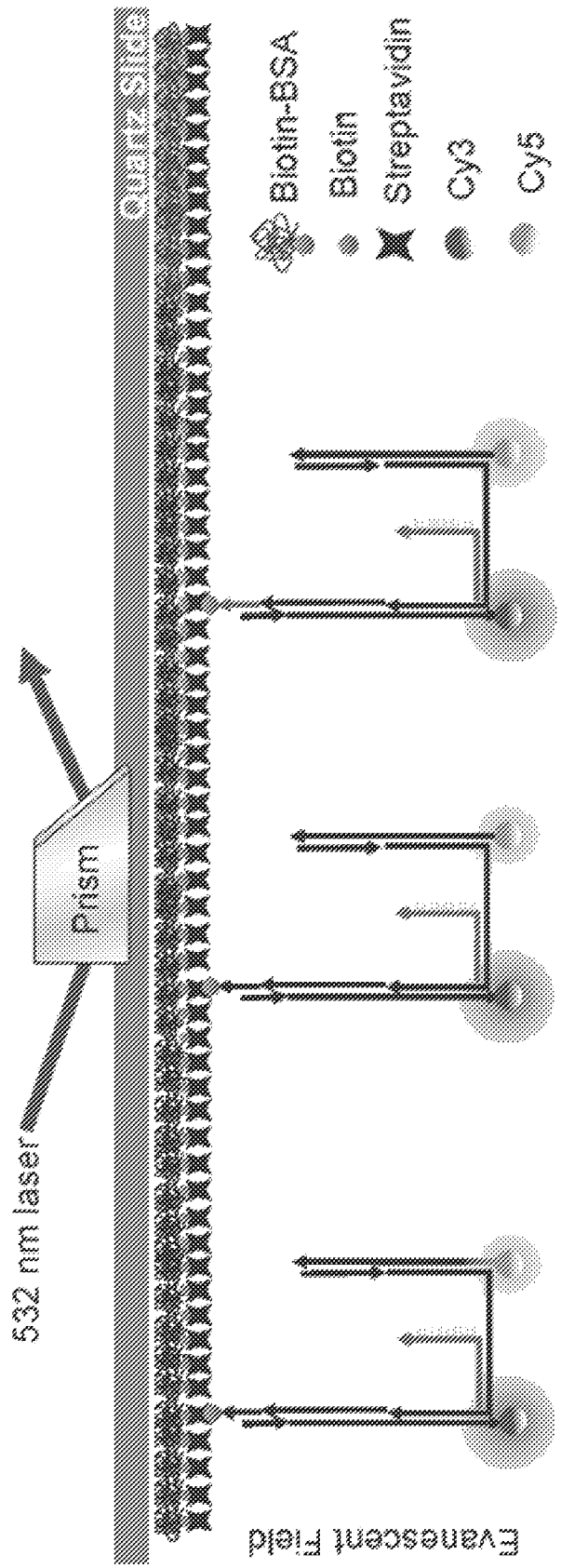
Figure 2A:
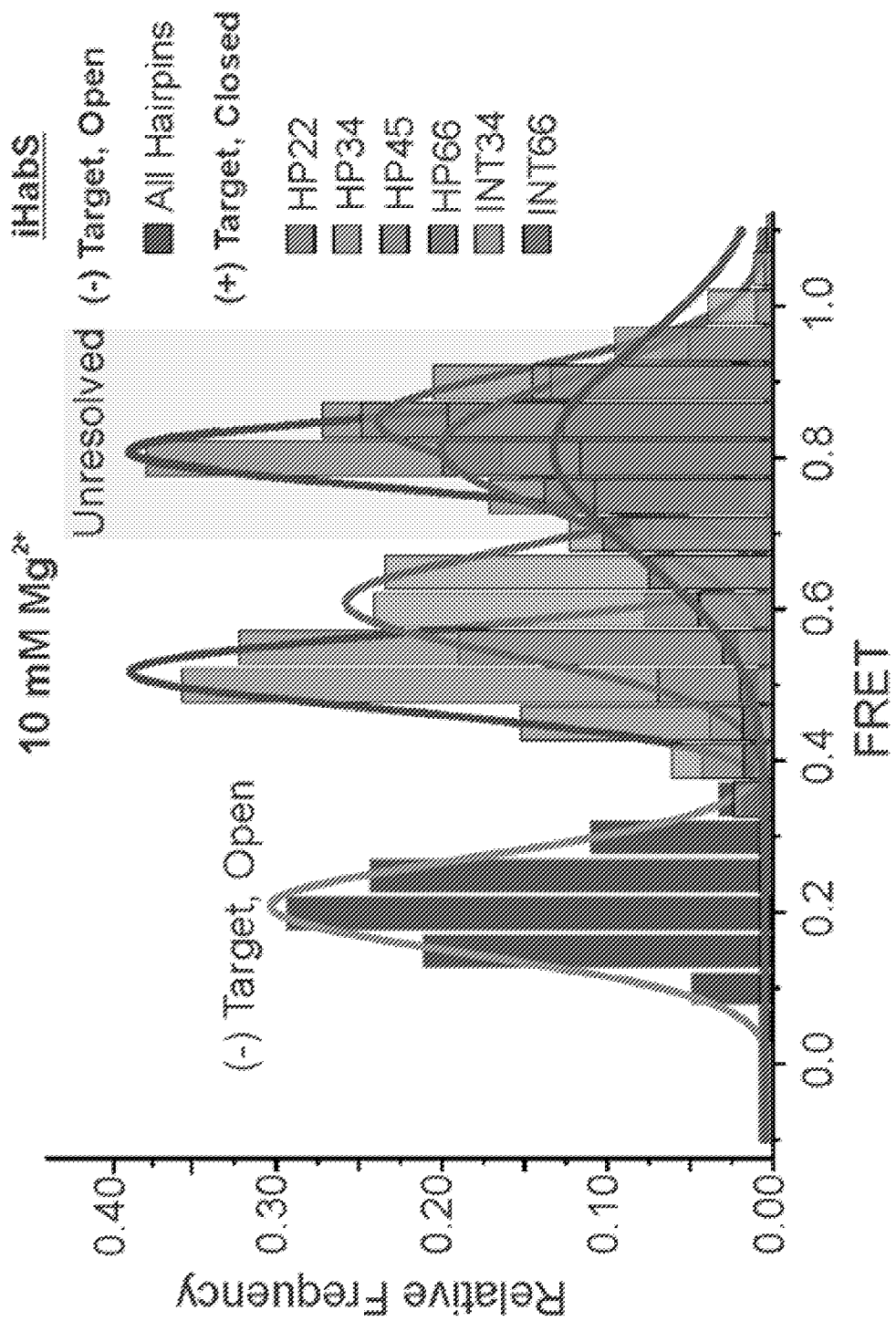
FIGS. 2A to 2C show smFRET characterization of iHabSs under different concentrations of $Mg^{2+}$.
Figure 2B:
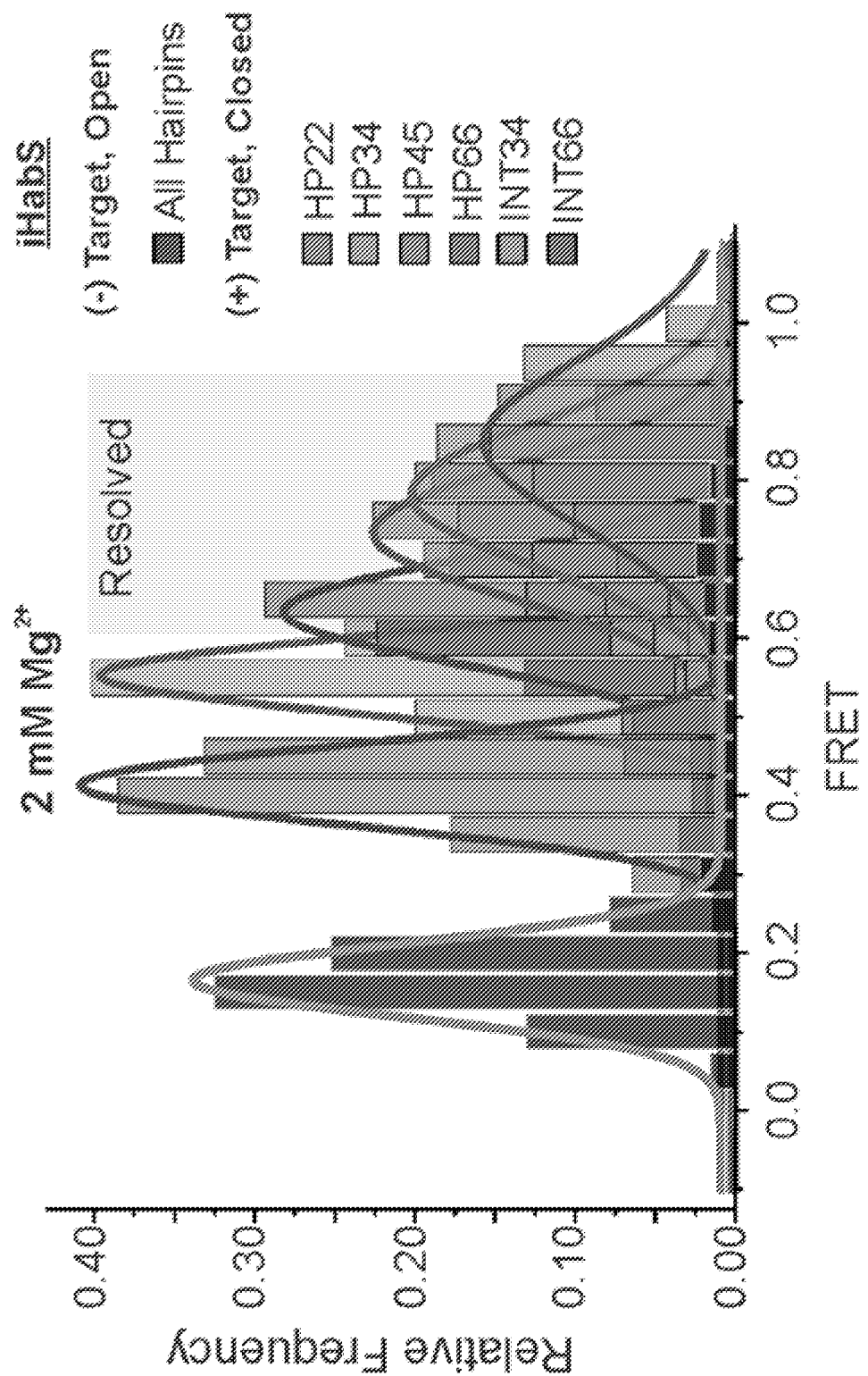
Figure 2C:
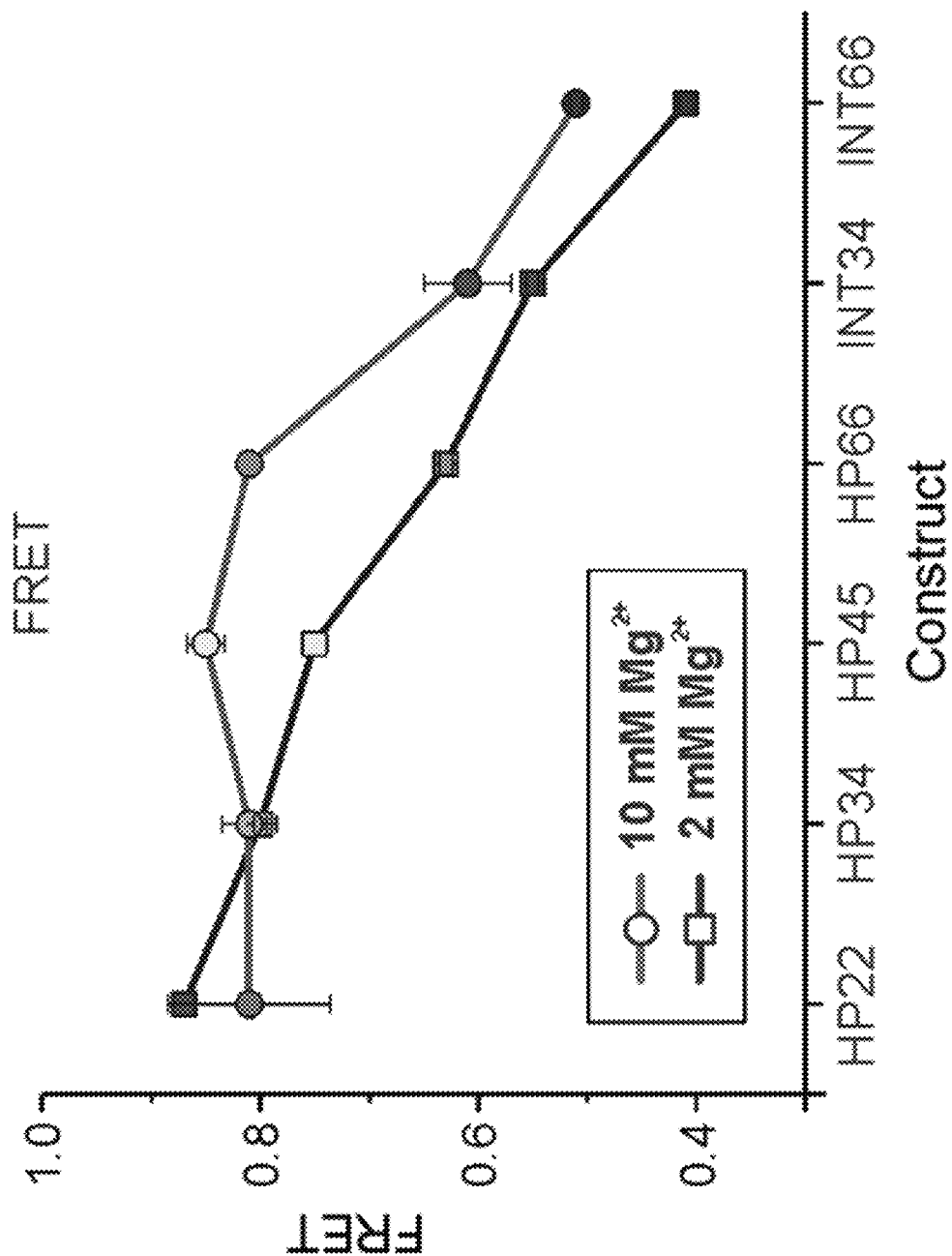
Figure 11B:
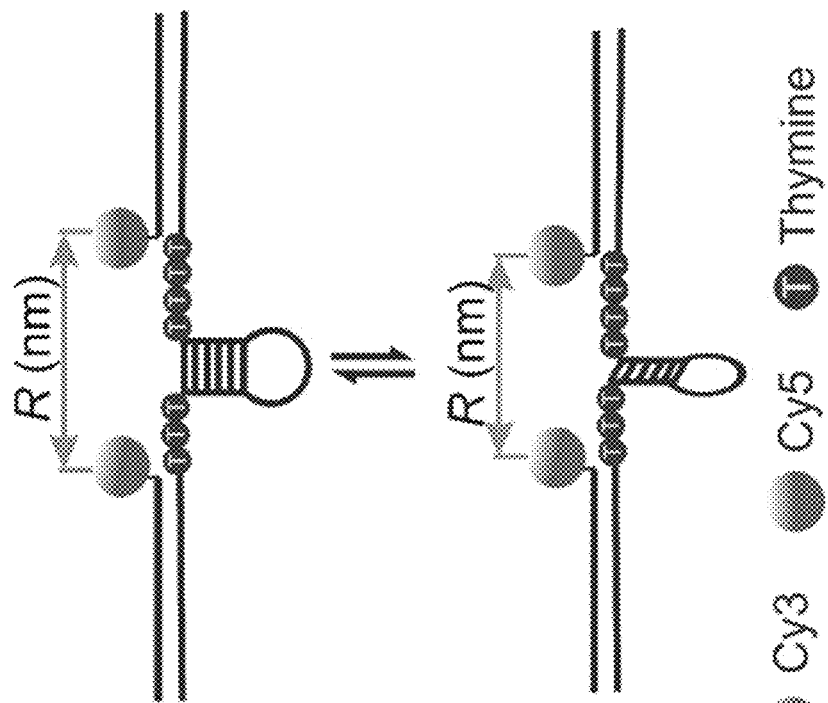

There initial FRET analyses were carried out in a 1×TAE buffer containing 10 mM $Mg^{2+}$ (pH 7.4). The FRET movies were processed using IDL and MATLAB codes (See Methods) and the FRET efficiencies were calculated as $I_A/(I_D+I_A)$, where $I_A$ and $I_D$ represent the background-corrected fluorescence intensities of the acceptor (Cy5) and donor (Cy3), respectively. As expected, all iHabSs show a low FRET value (~0.2) in their open conformations regardless of the length of thymine-spacers and the fluorophore labeling schemes—terminal or internal ("INT") (FIGS. 1, 2, 10). It was expected that the FRET values of iHabSs in their closed conformations rely on the spacer-length (the longer the spacer the lower the FRET). However, all of the terminally labeled iHabSs (HP22, HP34, HP45, and HP66) showed no difference in the FRET values (~0.80, FIG. 2a). This observation indicated that the inter-dye distance is apparently the same in these four iHabSs. This observation was attributed to compaction of single-stranded spacers at 10 mM $Mg^{2+}$ due to electrostatic shielding, thereby mitigating the effect of spacers (Newby Lambert, M., et al. (2006) Biophysical Journal 90:3672-3685). The same experiments performed at a lower, more biologically relevant, concentration of $Mg^{2+}$ (2 mM) show spacer-dependent FRET of iHabSs (FIG. 2B), confirming that the 2 mM $Mg^{2+}$ provides resolvable FRET values for all six iHabSs. It is important to note that, due to the presence of 1 mM EDTA in the 1×TAE buffer, the effective concentration of $Mg^{2+}$ in these experiments can be <2 mM due to chelation. When the mean FRET values under the two different concentrations of $Mg^{2+}$ were compared, there was no correlation between the FRET and spacer-length at 10 mM $Mg^{2+}$ except for the internally labeled iHabSs, however a nice correlation was observed for all iHabSs at 2 mM $Mg^{2+}$ (FIG. 2C). Further, this correlation was consistent with the FRET-trend calculated for different spacer lengths (see Table 3, FIG. 11 for calculation details). Therefore, 2 mM $Mg^{2+}$ was used for the rest of the experiments. Among the six possible iHabSs tested here, HP22, HP66, and INT66 were selected for multiplexing experiments as they exhibit distinct FRET values (HP22: 0.85, HP66: 0.65, and INT66: 0.40).

TABLE 3

FRET values calculated based on the expected inter-dye distance of fluorophores on an iHabS sensor containing various DNA oligonucleotide (nt) spacers.

| # of nt spacers | Inter-dye distance (R) | Expected FRET |
| --- | --- | --- |
| 0 | 1* | 1.000 |
| 1 | 1.43 | 1.000 |
| 2 | 1.86 | 0.998 |
| 3 | 2.29 | 0.994 |
| 4 | 2.72 | 0.984 |
| 5 | 3.15 | 0.962 |
| 6 | 3.58 | 0.922 |
| 7 | 4.01 | 0.856 |
| 8 | 4.44 | 0.764 |
| 9 | 4.87 | 0.650 |
| 10 | 5.3 | 0.528 |
| 11 | 5.73 | 0.412 |
| 12 | 6.16 | 0.312 |
| 13 | 6.59 | 0.232 |
| 14 | 7.02 | 0.172 |
| 15 | 7.45 | 0.127 |

TABLE 3-continued

FRET values calculated based on the expected inter-dye distance of fluorophores on an iHabS sensor containing various DNA oligonucleotide (nt) spacers.

| # of nt spacers | Inter-dye distance (R) | Expected FRET |
| --- | --- | --- |
| 16 | 7.88 | 0.094 |
| 17 | 8.31 | 0.070 |
| 18 | 8.74 | 0.053 |
| 19 | 9.17 | 0.040 |
| 20 | 9.6 | 0.031 |
| 21 | 10.03 | 0.024 |
| 22 | 10.46 | 0.018 |
| 23 | 10.89 | 0.015 |
| 24 | 11.32 | 0.012 |
| 25 | 11.75 | 0.009 |
| 26 | 12.18 | 0.008 |
| 27 | 12.61 | 0.006 |
| 28 | 13.04 | 0.005 |
| 29 | 13.47 | 0.004 |
| 30 | 13.9 | 0.003 |

*An average of 1 nm length is assumed for distance added by the hairpin stem (see Supplementary FIG. 5 for details).

Sensors' Recyclability

Figure 3A:
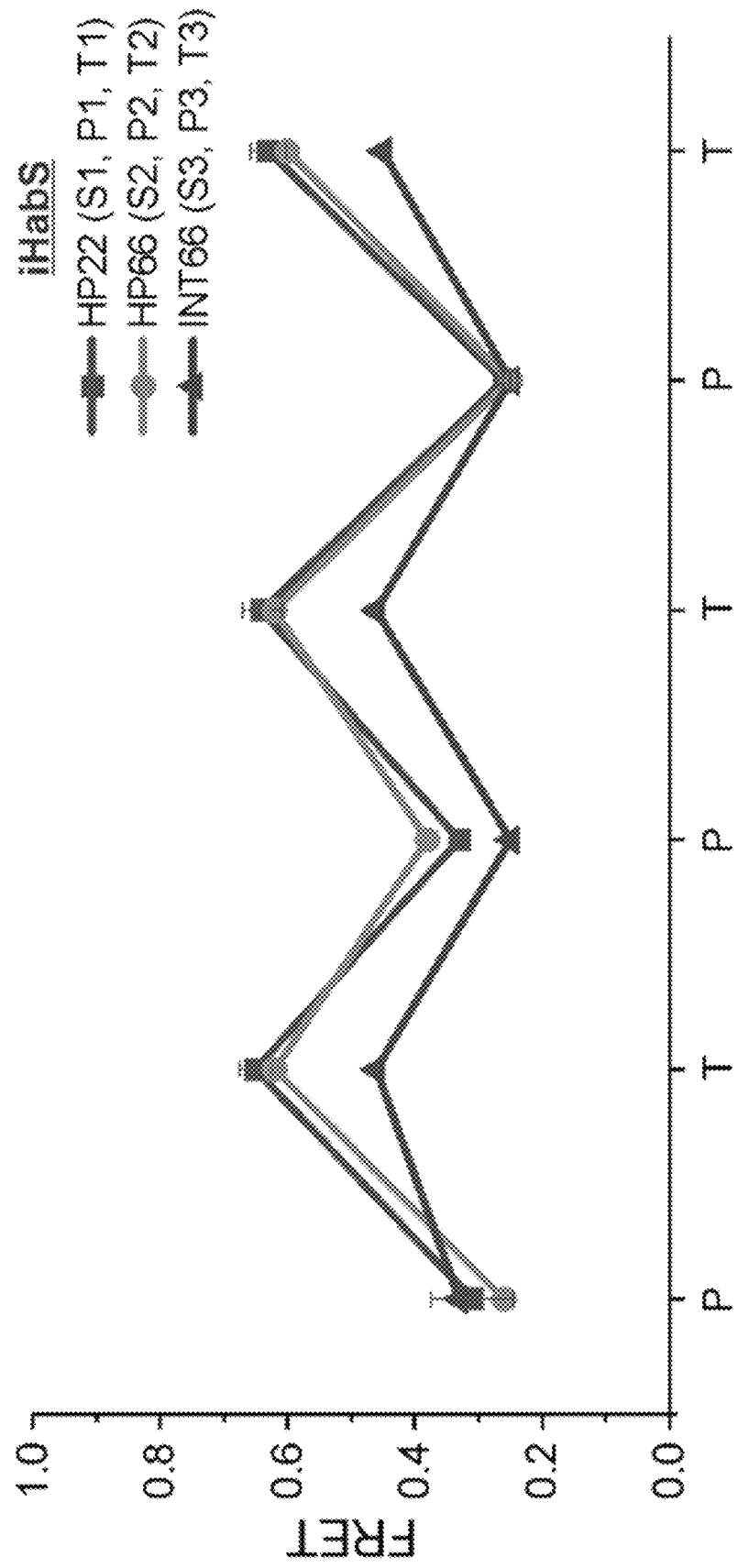
FIGS. 3A to C show recyclable iHabSs.
Figure 3B:
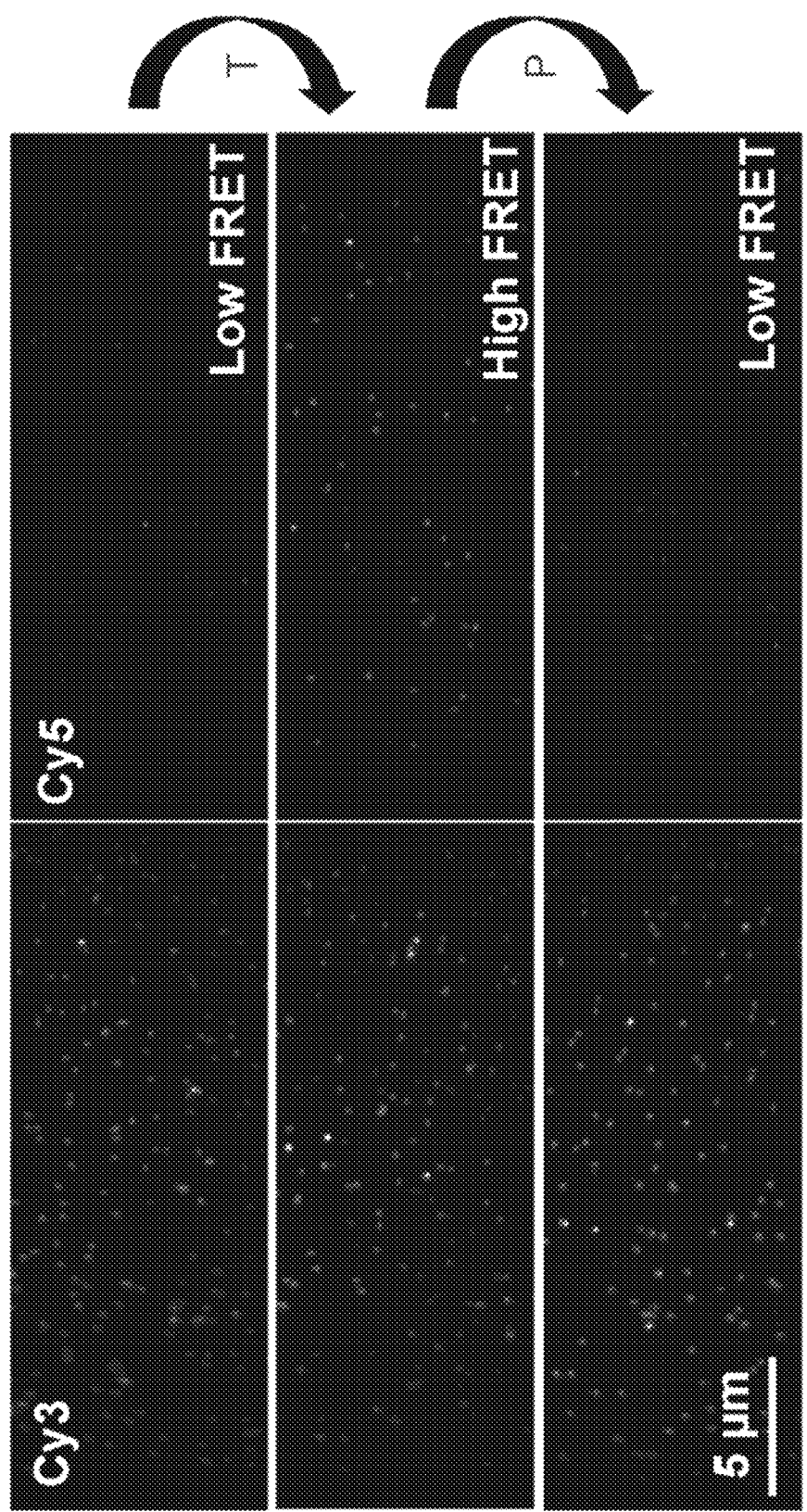
Figure 3C:
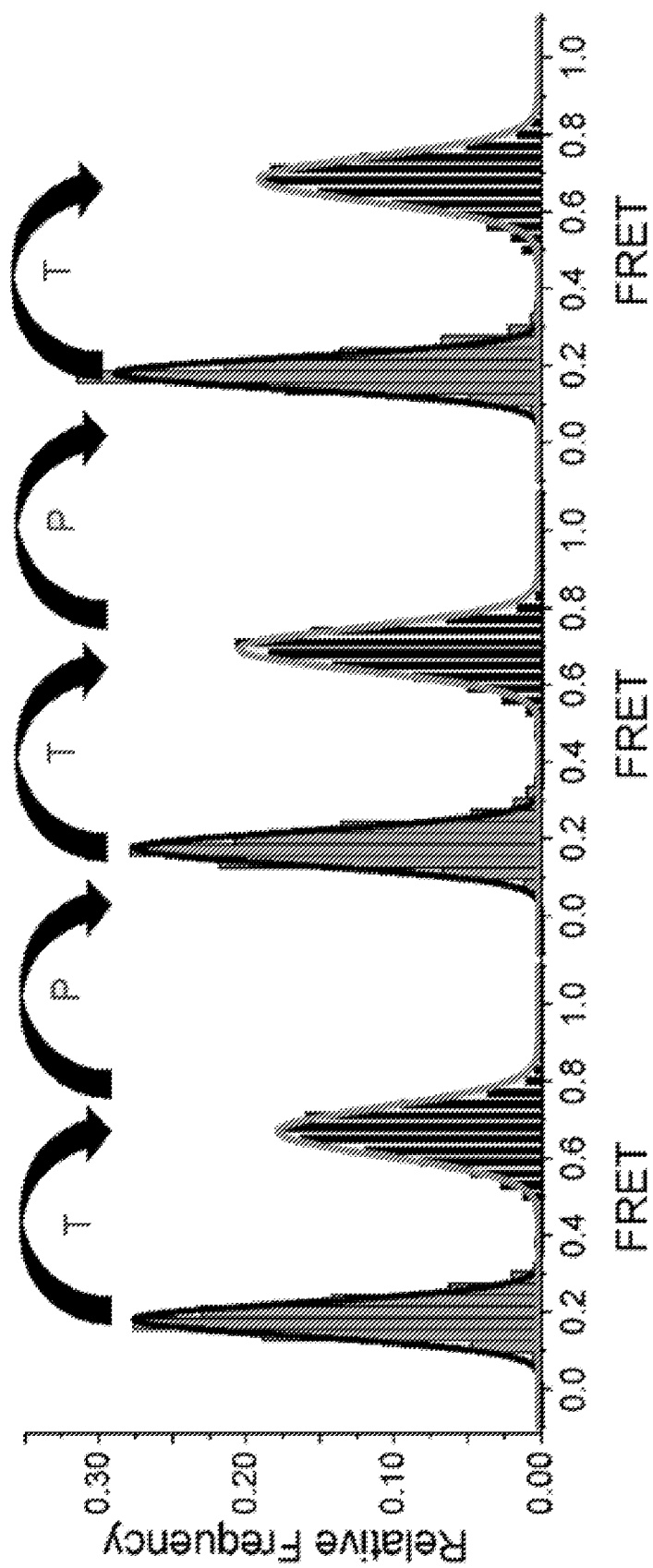

One of the most desired properties of sensors is their ability to be recycled. the recyclability of the iHabSs was characterized using both bulk and single-molecule FRET analyses (FIG. 3). In the bulk analysis, all iHabSs (HP22, HP66, and INT66) show a low-FRET state when open and a high-FRET state when closed (FIG. 3A). While the INT66 showed a distinctly different high-FRET state than those of HP22 and HP66, there was no clear correlation between the FRET and the spacer length in the latter two iHabSs which had been observed in the smFRET experiments (FIG. 2C). This observation was attributed to averaging of the FRET signals in bulk experiments while the smFRET technique allows selection of only those molecules that are fully formed and possess both fluorophores. More interestingly, for each iHabS, there was no apparent change in the FRET values even after multiple rounds of recycling. The full recyclability of the sensors was further confirmed by smFRET analysis of one of the constructs, HP66, which shows highly reproducible low- and high-FRET values (FIGS. 3B and 3C) (tested up to 3 cycles). Taken together, these results support that the iHabSs are fully functional and recyclable as designed, demonstrating that they offer an economic and efficient detection.

Figures 4A, 4B:
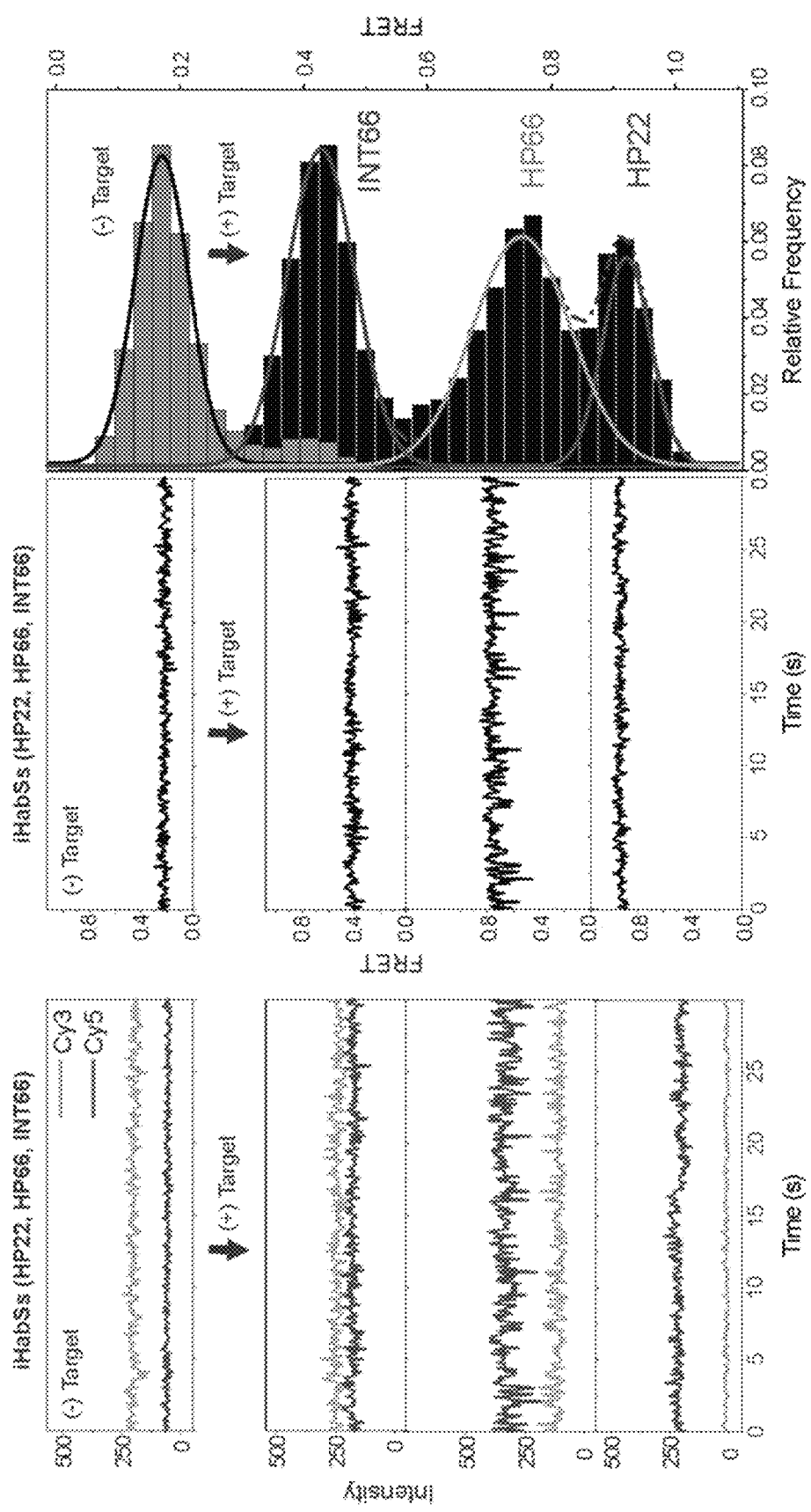
FIGS. 4A and 4B shows method validation through simultaneous imaging of three iHabSs.

Multiplexed Sensing
Method Validation:

Towards developing a multiplex platform, a homogenous type (mix and measure) assay containing three iHabSs differing in the spacer lengths was performed while keeping everything else (hairpin, probe, and target sequences) the same. The pre-mixed iHabSs that are designed to detect the same target were surface immobilized on the quartz slide, imaged in the absence of targets, and re-imaged after 20 min of incubation with 1 micromolar (µM) target. The typical intensity-time traces, the corresponding FRET trajectories, and the overall FRET histograms are shown in FIG. 4. Upon plotting the histograms, a common low-FRET population centered at 0.17 was observed in the absence of target, however, three distinct FRET populations centered at 0.43, 0.75, and 0.92 were observed in the presence of target (FIG. 4). Each population in the FRET histogram was then assigned to the most likely iHabS based on the expected FRET. This assignment is in good agreement with the experimentally observed FRET values for these iHabSs when imaged individually in the same buffer (FIG. 2B).

Based on the negative control (gray histograms in FIGS. 2 & 4), we estimated that there is ~4% chance of getting a false positive signal perhaps due to missing probe strands during the assembly step. Interestingly, no such false-positive peaks were observed when iHabSs were recycled on the microscope slide (FIG. 3C), showing that the false-positives can be completely eliminated in this approach by in-situ recycling of iHabSs on the microscope slide (FIG. 3C). Taken together, the multiplexing approach with iHabSs can provide a background-free detection of nucleic acids.

Figure 5B:
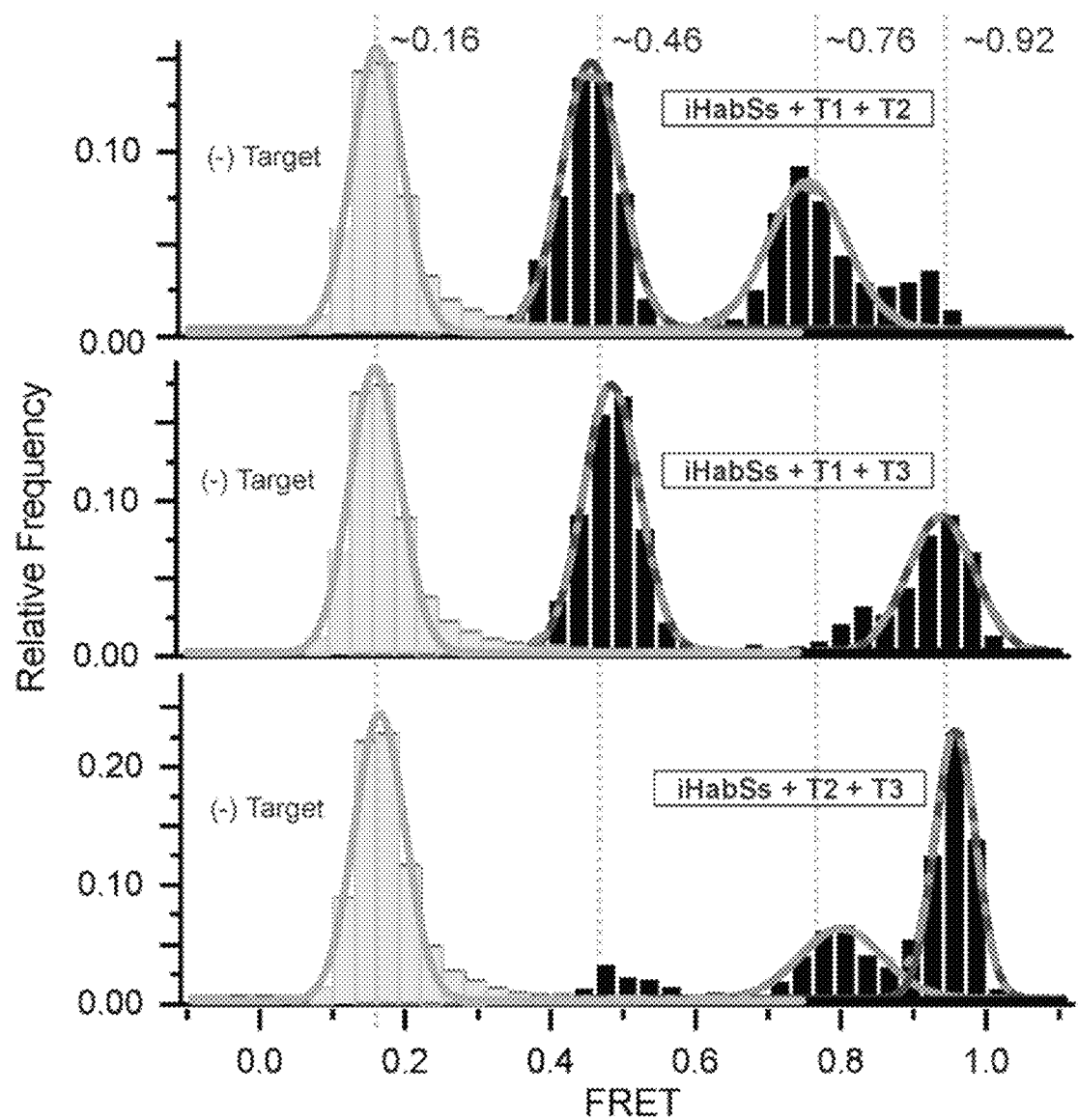

Multiplexing and Accuracy of Detection:

Next, a more rigorous characterization of the system for its ability to detect multiple targets in one experiment was performed by taking advantage of the unutilized spaces in conventional FRET histograms (FIG. 1A). To meet this purpose, target-specific iHabSs were designed by changing the hairpin and probe sequences. The experiments were performed as in FIG. 4 except all three targets were being used simultaneously this time. The histogram indeed showed three distinct FRET populations (FIG. 5A) with the mean FRET values consistent with what was observed in FIG. 4B. These results clearly demonstrated an excellent performance of the iHabSs in multiplexing. Additionally, to validate the accuracy of detection and to check for the potential crosstalk due to nonspecific binding of the targets, smFRET experiments were performed in the presence of two targets while all three iHabSs were immobilized (FIG. 5B). Each combination of targets (T1+T2, T1+T3, and T2+T3) yielded only two peaks in the histograms, validating that the approach can accurately detect targets as designed. Additionally, a clear high-FRET peak was observed after 20 min incubation of surface immobilized iHabSs with the target molecules, suggesting a rapid detection. It was estimated that the total time needed per analysis is less than 5 hr.

Analytical Sensitivity of iHabSs:

Finally, the sensitivity of the approach was determined by acquiring a series of smFRET histograms for one of the iHabSs (HP66) at different concentrations of target (FIG. 6A). By comparing the area under the curve (AUC) of the high FRET population to that of the low FRET population a clear correlation was observed between the high-FRET fraction and target concentration. The data were essentially linear up to approximately 2.5 nM, above which the response was curved and plateaued (FIG. 12). The calculated limit of detection (LOD), defined as $3 \times s.d._{blank}$/slope, was 183 pM. The raw AUC values of the high FRET populations at different target concentrations were also examined and showed a similar linear trend over the same concentration range with an LOD of 199 pM (FIG. 6B). These results show that the AUC values can be directly used to quantitate target concentrations. This is particularly important in multiplexing where a direct assessment of the low FRET peak is not feasible as all iHabSs share the same low FRET (~0.2) peak. However, when AUC is used to create a calibration curve, the number of molecules for each concentration on the curve should remain constant (serving as a normalizing factor) for an accurate quantification of targets in the multiplex assay. The LODs for either approach are in the range of typical nucleic acid biomarker concentrations (low pM to low nM) (Wang, K., et al. (2012) PLoS ONE 7:e41561) such as the circulating miRNAs reported in various types of cancers (Mo, M.-H., et al. (2012) J Cancer 3:432-448; Iorio, M. V., et al. (2012) EMBO Mol Med. 4:143-159).

Specificity of iHabSs.

Finally, the ability of the sensors to discriminate against single-base mismatch sequences was investigated (Zhang, D. Y., et al. Nat. Chem. (2012) 4:208-214; Broadwater, D. W. B., Jr., et al. Biophys. J. (2016) 110:1476-1484; Zhou, X. et al. Langmuir (2018) 34:14811-14816; Wang, X., et al. Biosens. Bioelectron. (2013) 41:569-575) from perfectly complementary targets both individually and when multiplexed (FIG. 13). Previous studies have shown that tuning the toehold length and mismatch position provides a higher discrimination between single-base mismatch and fully complementary target (Wang, X., et al. Biosens. Bioelectron. (2013) 41:569-575; Zhang, Z., et al. Small (2010) 6:1854-1858). While the individual sensors (HP22, HP66, and INT66) showed an efficient closing of the hairpin in the presence of their corresponding complementary targets as evidenced by a large high-EFRET population for the respective sensors (FIG. 13A, middle panel)), using previously optimized conditions (6-base toehold with inner-end mutation) (Zhang, Z., et al. Small (2010) 6:1854-1858; Wang, X., et al. Biosens. Bioelectron. (2013) 41:569-575) no significant high-EFRET population for single-base mismatch targets was observed (FIG. 13A, right panel). The lack of the high-EFRET population in the presence of a saturating concentration of mutants (5 nM) demonstrated the sensors' ability to discriminate against single-base mismatch sequences. Further, by determining the fraction of high-EFRET population in the absence of fully complementary target ("(-)Target", left panel, FIG. 13A), we determined that the average background is 3±2% (FIG. 13B). Similar analysis in the presence of single-base mismatch target ("(+)Mutant", right panel, FIG. 13A), no false positives were observed (horizontal dotted line in FIG. 13B identifies the average background and the high EFRET fraction above the background represents false positives) for INT66 and HP66 and <5% for HP22. As expected, three distinct high-EFRET populations were observed for multiplexed detection of the three targets; however, no significant high-EFRET populations were observed in the presence of all three mutants (FIG. 13A, bottom panel). These results clearly demonstrate that, after the background correction, there is little to no signal for single-base mismatch sequences, showing a high specificity of the iHabSs.

CONCLUSION

The multiple detection approach described here constitutes interconvertible hairpin-based sensors (iHabSs) that have the potential to revolutionize conventional FRET studies. Compelling features of the approach are that the sensors have a straightforward design, are fully recyclable, allow high-confidence multiplex detection of target molecules without requiring more than one FRET pair, and there is no need to modify or label the target molecules. In addition, detection is rapid and highly sensitive down to a picomolar (pM) concentration of oligonucleotide targets. Since DNA/RNA hybrids exhibit a higher thermodynamic stability than that off the DNA-DNA duplexes, these iHabSs could enable ultrasensitive detection of miRNA biomarkers (Mo, M.-H., et al. (2012) J Cancer 3:432-448; Iorio, M. V., et al. (2012) EMBO Mol Med. 4:143-159; Wang, K., et al. (2012) PLoS ONE 7:e41561) via an efficient strand-displacement reaction. Additionally, these iHabSs have the potential to simultaneously detect at least six targets in a two-step (3+3) fashion, therefore, these iHabSs can facilitate the development of high-throughput detection platforms. The iHabSs developed here are not only attractive for the detection of multiple analytes in a single assay but also for biomarker assays in complex biological matrices for the assessment of many diseases and have potential applications in many other areas of sensing. Incorporation of photostable fluorophores into these recyclable iHabSs, which is quite possible with recent progress in creating new generation of organic dyes, can rapidly advance the field of multiplexing.

Methods

Materials.

Tris(hydroxymethyl)-aminomethane (Tris), acetic acid, ethylenediaminetetraacetic acid disodium salt (EDTA), magnesium chloride hexahydrate, 6-hydroxy-2,5,7,8-tetramethylchroman-2-carboxylic acid (Trolox), and protocatechuate 3,4-dioxygenase (PCD) were purchased from Fisher Scientific. Streptavidin and protocatechuic acid (PCA) were purchased from VWR. Biotinylated bovine serum albumin was purchased from Thermo Scientific. All DNA strands were purchased from Integrated DNA Technologies (IDT), Inc. and were reconstituted with filtered sterile water to a final stock concentration of 100 μM.

DNA Constructs.

In order to form the DNA constructs, constituent ssDNA oligos (Table 1) were thermally annealed at 1 μM concentrations in 1×TAE-Mg buffer. (40 mM Tris, 20 mM acetic acid, 1 mM EDTA, 12.5 mM $Mg^{2+}$, pH 7.4). The thermal annealing was carried out by slowly ramping the temperature of the solution down from 95° C. to 4° C. in a thermal cycler (Table 2).

Bulk FRET Measurements:

Bulk fluorescence experiments to verify the recyclability of the constructs were performed using a DeNovix FX-11 fluorimeter at an excitation wavelength of 525 nm to collect fluorescence emission intensities at 565 nm-650 nm and 665 nm-740 nm for green and red emissions corresponding to a donor and acceptor pair, respectively. Samples were prepared at a 30 nM concentration in 1×TAE with 2 mM $MgCl_2$. The resulting fluorescence intensities were converted to FRET values using the following equation $FRET=I_A/(I_D+I_A)$, where $I_A$ is the acceptor (Cy5) intensity and $I_D$ is the donor (Cy3) intensity (Gibbs, D. R., et al. (2018) Biochemistry 57:3616-3624; Fu, J., et al. (2016) Nature Protocols 11:2243; Suddala, K. C., et al. (2018) Nature Commun. 9:1896).

Preparation of Surface-Functionalized Flow Cell.

For single molecule experiments, the flow cell was functionalized before injection of sample by sequential incubation with 1 mg/mL biotinylated BSA and 0.2 mg/mL streptavidin for 5 min and 2 min, respectively. The flow cell was flushed with ~300 μL of 1×TAE-Mg buffer.

Single Molecule Sample Preparation and Imaging.

The functionalized flow cell was injected with 20 pM biotinylated-DNA construct prepared in imaging buffer which consists of 1×TAE, oxygen scavenging system (2 mM Trolox, 5 mM PCA, 50 nM PCD) (Aitken, C. E., et al. (2008) Biophysical Journal 94:1826-1835; Fu, J., et al. (2016) Nature Protocols 11:2243), and the desired concentration of $MgCl_2$ and NaCl. For multiplexing experiments the molar ratio was optimized to be: HP22:HP66:INT66=2:1:4 where the total concentration of iHabSs is roughly 21 pM. Choice of this ratio of iHabSs comes from trial and error to resolve the three FRET populations (FIG. 4). The buffer conditions were also optimized by adding 150 mM NaCl on top of the regular 2 mM $Mg^{2+}$ to minimize the occasional dynamics observed between the low- and high-FRET states. The cell was flushed with imaging buffer after incubation of construct for 30 sec to remove unbound sample before movies were recorded. The Cy3 fluorophore was continuously excited using a 532 nm HeNe laser. Fluorescence emission from Cy3 and Cy5 fluorophores was simultaneously recorded through green and red channels (512×256 pixels) using an EMCCD camera at a 100 ms time resolution. Please see Single Molecule Fluorescence Microscopy section in the Supplementary Information for instrumentation details. The presence of an active FRET pair was confirmed at the end of each experiment by direct excitation with a 639 nm red laser (Gibbs, D. R., et al. (2018) Biochemistry 57:3616-3624).

Data Acquisition and Analysis.

Data acquisition was performed using Single.exe software available from TJ Ha Lab. Post processing of data was done by the use of IDL and MATLAB scripts acquired from the Center for the Physics of Living Cells at Illinois University (https://cplc.illinois.edu/software/). Briefly, only those molecules which provided evidence of both Cy3 and Cy5, as well as single-step photobleaching from all single molecule traces were chosen for subsequent analysis. The FRET histograms were prepared in Origin for the first 100 frames unless otherwise noted and fitted with Gaussian fittings. Standard deviations and averages for single molecule experiments were acquired by randomly assigning molecules to three groups and analyzing three histograms obtained for each group.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A hairpin-based sensor, comprising
a first single-stranded DNA oligonucleotide ("first oligo") having a 5' end and a 3' end and comprising a DNA hairpin region flanked by a 5' flanking region and a 3' flanking region;
a second single-stranded DNA oligonucleotide ("second oligo") having a 5' end and a 3' end and comprising a nucleic acid sequence complementary to at least a portion of the 3' flanking region;
a third single-stranded DNA oligonucleotide ("third oligo") having a 5' end and a 3' end and comprising a nucleic acid sequence complementary to at least a portion of the 5' flanking region;
a fourth single-stranded DNA oligonucleotide ("probe") having a 5' end and a 3' end, comprising a nucleic acid sequence complementary to at least a portion of the DNA hairpin region, and comprising a nucleic acid sequence complementary to at least a portion of a target single stranded DNA or RNA molecule;
a first fluorescent molecule conjugated to the second oligo; and a second fluorescent molecule conjugated to the third oligo;
wherein the first fluorescent molecule and the second fluorescent molecule together form a fluorescence resonance energy transfer (FRET) pair,
wherein the FRET pair emit at a first-FRET efficiency when the probe is binding the DNA hairpin region, and
wherein the FRET pair emit at a higher second-FRET efficiency when the probe binds the target DNA or RNA molecule, displacing the probe from the DNA hairpin region, allowing the DNA hairpin region to form a DNA hairpin, and shortening the distance between the first fluorescent molecule and the second fluorescent molecule.

2. The hairpin-based sensor of claim 1, wherein the first fluorescent molecule is conjugated to the 3' end of the second oligo.

3. The hairpin-based sensor of claim 1, wherein the second fluorescent molecule is conjugated to the 5' end of the third oligo.

4. The hairpin-based sensor of claim 1, wherein the FRET pair comprise Cy3 and Cy5.

5. The hairpin-based sensor of claim 1, further comprising a fifth single-stranded DNA oligonucleotide ("fifth oligo") having a 5' end and a 3' end and comprising a nucleic acid sequence complementary to at least a portion of the second oligo, wherein the 3' flanking region of the first oligo and the fifth oligo together form a complementary strand for the second oligo.

6. The hairpin-based sensor of claim 1, further comprising a sixth single-stranded DNA oligonucleotide ("sixth oligo") having a 5' end and a 3' end and comprising a nucleic acid sequence complementary to at least a portion of the third oligo, wherein the 5' flanking region of the first oligo and the sixth oligo together form a complementary strand for the third oligo.

7. The hairpin-based sensor of claim 1, further comprising a seventh single-stranded DNA oligonucleotide ("seventh oligo") having a 5' end and a 3' end and an eighth single-stranded DNA oligonucleotide ("eighth oligo") having a 5' end and a 3' end, wherein the seventh oligo comprises a nucleic acid sequence complementary to at least a portion of either the fifth or the sixth oligo and a nucleic acid sequence complementary to at least a portion of the eight oligo.

8. The hairpin-based sensor of claim 1, wherein the eight oligo is conjugated to a biotin molecule.

9. A multiplexed detection system, comprising a plurality of unique hairpin-based sensors according to claim 1, wherein each of the unique hairpin-based sensors has a unique probe designed to recognize a different DNA or RNA target molecule, wherein each of the unique hairpin-based sensors has a unique spacing between the first fluorescent molecule and the second fluorescent molecule when the DNA hairpin is formed, and wherein each of the unique hairpin-based sensors have the same FRET pair but emit a unique second-FRET efficiency.

10. The system of claim 9, wherein the hairpin-based sensors are attached to a microscope slide.

11. A method for detecting a DNA or RNA target molecule in a sample, comprising contacting the system of claim 9 with the sample under conditions suitable for DNA binding, exciting the FRET pair with a light source, and measuring FRET efficiency.

* * * * *

SEQUENCE LISTING

```
<160> NUMBER OF SEQ ID NOS: 31

<210> SEQ ID NO 1
<211> LENGTH: 40
<212> TYPE: DNA
<213> ORGANISM: Artificial Sequence
<220> FEATURE:
<223> OTHER INFORMATION: Synthetic Construct

<400> SEQUENCE: 1
tcttgtgaac tccctactat ccttaaacgc atatctctga                40
```

<210> SEQ ID NO 2
<211> LENGTH: 40
<212> TYPE: DNA
<213> ORGANISM: Artificial Sequence
<220> FEATURE:
<223> OTHER INFORMATION: Synthetic Construct

<400> SEQUENCE: 2
gtgtatgacc cctatatgtg agcttctgat gttacccgag                     40

<210> SEQ ID NO 3
<211> LENGTH: 40
<212> TYPE: DNA
<213> ORGANISM: Artificial Sequence
<220> FEATURE:
<223> OTHER INFORMATION: Synthetic Construct

<400> SEQUENCE: 3
atagtaggga gttcacaaga tgtataagca aatatttaaa                     40

<210> SEQ ID NO 4
<211> LENGTH: 30
<212> TYPE: DNA
<213> ORGANISM: Artificial Sequence
<220> FEATURE:
<223> OTHER INFORMATION: Synthetic Construct

<400> SEQUENCE: 4
ttgcatgcct gcaggtcgac tctagttttt                                30

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
ctcgggtaac atcagaagct                                           20

<210> SEQ ID NO 6
<211> LENGTH: 47
<212> TYPE: DNA
<213> ORGANISM: Artificial Sequence
<220> FEATURE:
<223> OTHER INFORMATION: Synthetic Construct

<400> SEQUENCE: 6
tcagaagctc tcatatagag gtcatacact aatcgagtag tgagttc             47

<210> SEQ ID NO 7
<211> LENGTH: 76
<212> TYPE: DNA
<213> ORGANISM: Artificial Sequence
<220> FEATURE:
<223> OTHER INFORMATION: Synthetic Construct

<400> SEQUENCE: 7
cacatatagg ggtcatacac ttgtttccta atatatataa agtgctatgg aaactttcag    60
agatatgcgt ttaagg                                               76

<210> SEQ ID NO 8
<211> LENGTH: 79
<212> TYPE: DNA
<213> ORGANISM: Artificial Sequence

```
<220> FEATURE:
<223> OTHER INFORMATION: Synthetic Construct

<400> SEQUENCE: 8
cacatatagg ggtcatacac tttgtttcct aatatatata aagtgctatg gaaactttt      60 cagagatatg cgtttaagg                                                  79

<210> SEQ ID NO 9
<211> LENGTH: 81
<212> TYPE: DNA
<213> ORGANISM: Artificial Sequence
<220> FEATURE:
<223> OTHER INFORMATION: Synthetic Construct

<400> SEQUENCE: 9
cacatatagg ggtcatacac ttttgtttcc taatatatat aaagtgctat ggaaactttt     60
ttcagagata tgcgtttaag g                                               81

<210> SEQ ID NO 10
<211> LENGTH: 84
<212> TYPE: DNA
<213> ORGANISM: Artificial Sequence
<220> FEATURE:
<223> OTHER INFORMATION: Synthetic Construct

<400> SEQUENCE: 10
cacatatagg ggtcatacac tttttttgttt cctaatatat ataaagtgct atggaaactt    60
tttttcagag atatgcgttt aagg                                            84

<210> SEQ ID NO 11
<211> LENGTH: 25
<212> TYPE: DNA
<213> ORGANISM: Artificial Sequence
<220> FEATURE:
<223> OTHER INFORMATION: Synthetic Construct

<400> SEQUENCE: 11
tttccatagc actttttaca tacct                                           25

<210> SEQ ID NO 12
<211> LENGTH: 25
<212> TYPE: DNA
<213> ORGANISM: Artificial Sequence
<220> FEATURE:
<223> OTHER INFORMATION: Synthetic Construct

<400> SEQUENCE: 12
aggtatgtaa aaagtgctat ggaaa                                           25

<210> SEQ ID NO 13
<211> LENGTH: 82
<212> TYPE: DNA
<213> ORGANISM: Artificial Sequence
<220> FEATURE:
<223> OTHER INFORMATION: Synthetic Construct

<400> SEQUENCE: 13
cacatatagg ggtcatacac tttttagca ctaatatata tttcaactac agtgcttttt      60
tttcagagat atgcgtttaa gg                                              82
```

<210> SEQ ID NO 14
<211> LENGTH: 25
<212> TYPE: DNA
<213> ORGANISM: Artificial Sequence
<220> FEATURE:
<223> OTHER INFORMATION: Synthetic Construct

<400> SEQUENCE: 14
agcactgtag ttgaagatgg ttcac                                    25

<210> SEQ ID NO 15
<211> LENGTH: 25
<212> TYPE: DNA
<213> ORGANISM: Artificial Sequence
<220> FEATURE:
<223> OTHER INFORMATION: Synthetic Construct

<400> SEQUENCE: 15
gtgaaccatc ttcaactaca gtgct                                    25

<210> SEQ ID NO 16
<211> LENGTH: 83
<212> TYPE: DNA
<213> ORGANISM: Artificial Sequence
<220> FEATURE:
<223> OTHER INFORMATION: Synthetic Construct

<400> SEQUENCE: 16
cacatatagg ggtcatacac tttttggtg gtaatatata tttgaaaagc agccacctt    60 ttttcagaga tatgcgttta agg                                      83

<210> SEQ ID NO 17
<211> LENGTH: 25
<212> TYPE: DNA
<213> ORGANISM: Artificial Sequence
<220> FEATURE:
<223> OTHER INFORMATION: Synthetic Construct

<400> SEQUENCE: 17
agcactgtag ttgaagatgg ttcac                                    25

<210> SEQ ID NO 18
<211> LENGTH: 25
<212> TYPE: DNA
<213> ORGANISM: Artificial Sequence
<220> FEATURE:
<223> OTHER INFORMATION: Synthetic Construct

<400> SEQUENCE: 18
gtgaaccatc ttcaactaca gtgct                                    25

<210> SEQ ID NO 19
<211> LENGTH: 21
<212> TYPE: DNA
<213> ORGANISM: Artificial Sequence
<220> FEATURE:
<223> OTHER INFORMATION: Synthetic Construct

<400> SEQUENCE: 19
gtggctgctt ttcaactgtt g                                        21

<210> SEQ ID NO 20
<211> LENGTH: 21
<212> TYPE: DNA
<213> ORGANISM: Artificial Sequence

```
<220> FEATURE:
<223> OTHER INFORMATION: Synthetic Construct

<400> SEQUENCE: 20
caacagttga aaagcagcca c                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic Construct

<400> SEQUENCE: 21
caacaattga aaagcagcca c                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic Construct

<400> SEQUENCE: 22
agcactgtag ttgaagatgg t                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic Construct

<400> SEQUENCE: 23
accatcttca actacagtgc t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic Construct

<400> SEQUENCE: 24
accattttca actacagtgc t                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic Construct

<400> SEQUENCE: 25
tttccatagc acttttaca t                                               21

<210> SEQ ID NO 26
<211> LENGTH: 21
<212> TYPE: DNA
<213> ORGANISM: Artificial Sequence
<220> FEATURE:
<223> OTHER INFORMATION: Synthetic Construct

<400> SEQUENCE: 26
atgtaaaaag tgctatggaa a                                              21
```

```
<210> SEQ ID NO 27
<211> LENGTH: 21
<212> TYPE: DNA
<213> ORGANISM: Artificial Sequence
<220> FEATURE:
<223> OTHER INFORMATION: Synthetic Construct

<400> SEQUENCE: 27
atgtagaaag tgctatggaa a                                                   21

<210> SEQ ID NO 28
<211> LENGTH: 36
<212> TYPE: DNA
<213> ORGANISM: Artificial Sequence
<220> FEATURE:
<223> OTHER INFORMATION: Synthetic Construct

<400> SEQUENCE: 28
ttgtttccta atatatataa agtgctatgg aaactt                                   36

<210> SEQ ID NO 29
<211> LENGTH: 38
<212> TYPE: DNA
<213> ORGANISM: Artificial Sequence
<220> FEATURE:
<223> OTHER INFORMATION: Synthetic Construct

<400> SEQUENCE: 29
tttgtttcct aatatatata aagtgctatg gaaactttt                                38

<210> SEQ ID NO 30
<211> LENGTH: 40
<212> TYPE: DNA
<213> ORGANISM: Artificial Sequence
<220> FEATURE:
<223> OTHER INFORMATION: Synthetic Construct

<400> SEQUENCE: 30
ttttgtttcc taatatatat aaagtgctat ggaaacttt                                40

<210> SEQ ID NO 31
<211> LENGTH: 42
<212> TYPE: DNA
<213> ORGANISM: Artificial Sequence
<220> FEATURE:
<223> OTHER INFORMATION: Synthetic Construct

<400> SEQUENCE: 31
tttttgtttc ctaatatata taaagtgcta tggaaacttt tt                            42
```